US009753047B2

(12) United States Patent
Cooney et al.

(10) Patent No.: US 9,753,047 B2
(45) Date of Patent: Sep. 5, 2017

(54) ROTATING SAMPLE POSITIONING APPARATUS

(71) Applicant: AKONNI BIOSYSTEMS INC., Frederick, MD (US)

(72) Inventors: Christopher Cooney, Severn, MD (US); Alexander Perov, Germantown, MD (US); Arial Bueno, Frederick, MD (US); Charles Daitch, New Market, MD (US)

(73) Assignee: AKONNI BIOSYSTEMS INC., Frederick, MD (US)

( * ) Notice: Subject to any disclaimer, the term of this patent is extended or adjusted under 35 U.S.C. 154(b) by 0 days.

(21) Appl. No.: 14/922,892

(22) Filed: Oct. 26, 2015

(65) Prior Publication Data

US 2016/0116495 A1 Apr. 28, 2016

Related U.S. Application Data

(60) Provisional application No. 62/069,112, filed on Oct. 27, 2014.

(51) Int. Cl.
*G01N 35/02* (2006.01)
*G01N 35/00* (2006.01)
G01N 35/04 (2006.01)
G01N 21/64 (2006.01)

(52) U.S. Cl.
CPC ..... *G01N 35/025* (2013.01); *G01N 35/00029* (2013.01); *G01N 21/6452* (2013.01); *G01N 21/6458* (2013.01); *G01N 2035/00158* (2013.01); *G01N 2035/00346* (2013.01); *G01N 2035/00495* (2013.01); *G01N 2035/00534* (2013.01); *G01N 2035/0446* (2013.01); *G01N 2035/0449* (2013.01); *G01N 2035/0465* (2013.01)

(58) Field of Classification Search
CPC .......... G01N 2035/00049; G01N 2035/00158; G01N 2035/00495
See application file for complete search history.

(56) References Cited

U.S. PATENT DOCUMENTS

| 5,103,338 A | 4/1992 | Crowley et al. |
| 5,257,128 A | 10/1993 | Diller et al. |
| 5,367,401 A | 11/1994 | Saulietis |
| 5,863,504 A | 1/1999 | Heffelfinger et al. |
| 6,582,962 B1 | 6/2003 | Richards et al. |

(Continued)

OTHER PUBLICATIONS

International Search Report, International Preliminary Report on Patentability and Written Opinion, issued in Patent Application No. PCT/US2015/057378, mailed Jan. 19, 2016.

(Continued)

*Primary Examiner* — P. Kathryn Wright
(74) *Attorney, Agent, or Firm* — Michael Ye; Andrews Kurth Kenyon LLP

(57) ABSTRACT

A positioning system for a sample analysis device is disclosed. The positioning system comprises (1) a carousel comprising a platform and a sample loading tray mounted on the platform, and (2) a stage comprising a positioning system for positioning the carousel under the optical path of an imaging system. The sample loading tray is configured for holding a cartridge comprising one or more lateral flow cells (LFCs).

9 Claims, 26 Drawing Sheets

(56) References Cited

U.S. PATENT DOCUMENTS

| | | |
|---|---|---|
| 6,656,428 B1 | 12/2003 | Clark et al. |
| 2002/0114738 A1* | 8/2002 | Wyzgol ................ B01L 3/5027 422/509 |
| 2006/0160210 A1* | 7/2006 | Mori ................ B01L 3/502753 435/287.2 |
| 2009/0139311 A1 | 6/2009 | Lehto et al. |

OTHER PUBLICATIONS

Leland, Diane S., et al., "Role of Cell Culture for Virus Detection in the Age of Technology," Clinical Microbiology Reviews, Jan. 2007, vol. 20, No. 1, pp. 49-78.

\* cited by examiner

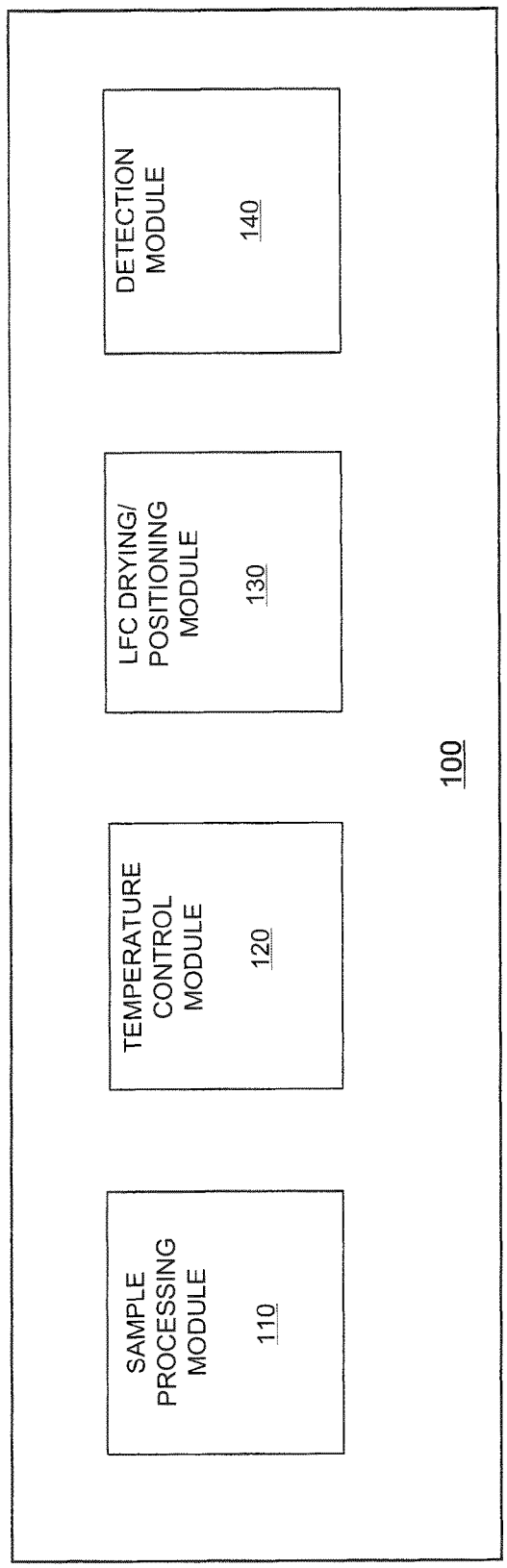

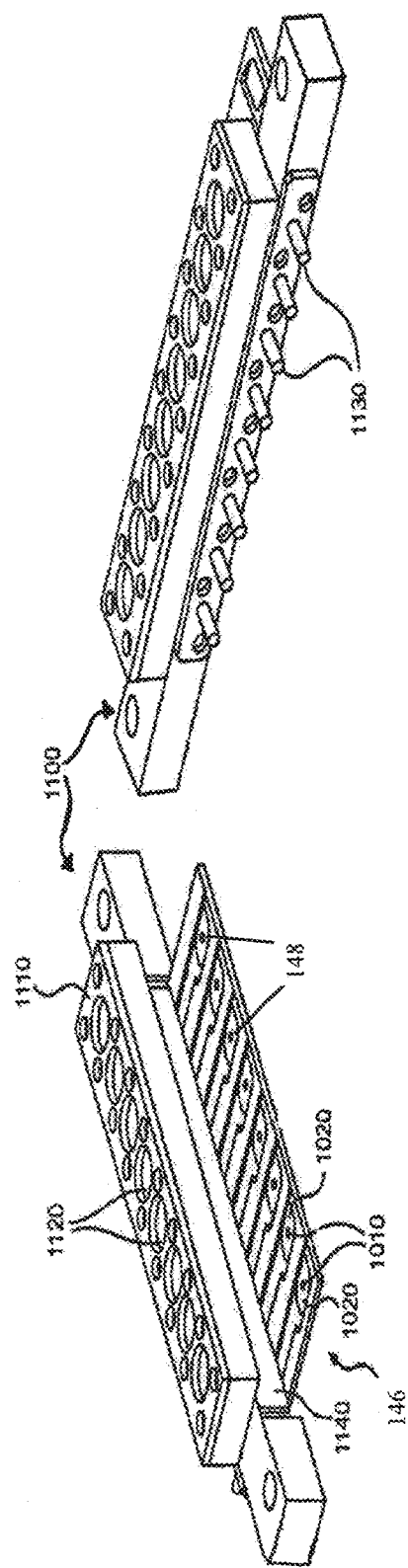

ROTATING SAMPLE POSITIONING APPARATUS

RELATED APPLICATIONS

This Application claims priority of U.S. Provisional Application No. 62/069,112, filed on Oct. 27, 2014, which is incorporated herein in its entirety by reference.

FIELD

The present application relates generally to sample analysis systems and, in particular, to a lateral flow cell positioning system for use in a sample-to-answer analysis system for detection of biological materials in a sample.

BACKGROUND

Molecular testing is a test designed to detect and identify biological materials, such as DNA, RNA and/or proteins, in a test sample. Molecular testing is beginning to emerge as a gold standard due to its speed, sensitivity and specificity. For example, molecular assays were found to be 75% more sensitive than conventional cultures when identifying enteroviruses in cerebrospinal fluid and are now considered the gold standard for this diagnostic (Leland et al., Clin. Microbiol Rev. 2007, 20:49-78)

Molecular assays for clinical use are typically limited to identification of less than six genetic sequences (e.g., real-time PCR assays). Microarrays, which are patterns of molecular probes attached to a solid support, are one way to increase the number of sequences that can be uniquely identified. The microarray analysis workflow often includes an expensive scanner for extracting fluorescence intensity information from the microarray elements. Microarray imaging may show improved signal-to-noise ratios when water is removed from the microarray elements (i.e, when the microarray is dried). Therefore, there is a need for developing simpler, more efficient and more cost effective methods and devices for performing molecular tests using microarray technology.

SUMMARY

In one aspect, a Lateral Flow Cell (LFC) positioning system for a sample analysis device includes (1) a carousel comprising a platform and a sample loading tray mounted on the platform, and (2) a stage comprising a positioning system for positioning said carousel, wherein the sample loading tray is configured for holding a cartridge comprising one or more LFCs. In some embodiments, the carousel is movable relative to the stage. In other embodiments, the carousel is rotatable relative to the stage.

In other embodiments, the carousel further comprises a clamp comprising a top bar, a bottom bar and at least one supporting rod connecting the top bar and the bottom bar. The platform and the sample loading tray are disposed between the top bar and the bottom bar of the clamp. The clamp is movable relative to the platform and is capable of securing a cartridge in the sample loading tray when the clamp is moved to a locked position.

In certain preferred embodiments, the stage includes a motor-driven rotor connected to the carousel to facilitate its rotation. Rotation of the carousel translates to a cartridge containing LFCs with typical rotational velocities in the range upwards of 200 rpm (e.g., 200-5000 rpm). This centrifugal force drives the water droplets within the reaction chambers toward an absorbent, leaving the reaction chamber in a dry state. Thus, microarray elements, including bound and/or amplified probes are retained in a dry state. Following the drying procedure, the rotational velocity of the carousel decreases and enters an indexing mode for imaging. During this mode, each of the reaction chambers indexes into position under a microarray imaging camera. An image is acquired, processed and analyzed. Then, the test result is reported.

Another aspect relates to an integrated sample analysis system. The system includes a sample purification device comprising a monolith that binds specifically to nucleic acids; a sample analysis device comprising a reaction chamber comprising a hydrophilic interior surface configured to hold a microarray comprising a plurality of nucleic acid-based probes; a temperature control module comprising heating and cooling elements to enable thermal exchange between said heating and cooling elements and the internal volume of said reaction chamber; an imaging device positioned to capture an image of said microarray in said reaction chamber; and an LFC positioning module as described herein.

Further aspects include methods for rotating and/or positioning the carousel of the present invention and to methods for detecting and analyzing probes bound to the microarrays in the LFCs of the present invention.

BRIEF DESCRIPTION OF DRAWINGS

For the purposes of this disclosure, unless otherwise indicated, identical reference numerals used in different figures refer to the same component.

FIG. 1 is a diagram of an exemplary sample detection system of the present application.

FIGS. 11A-11C show exemplary cartridges, which includes a Lateral Flow Array (LFA), which is an array of LFCs.

DETAILED DESCRIPTION

Figure 2A:
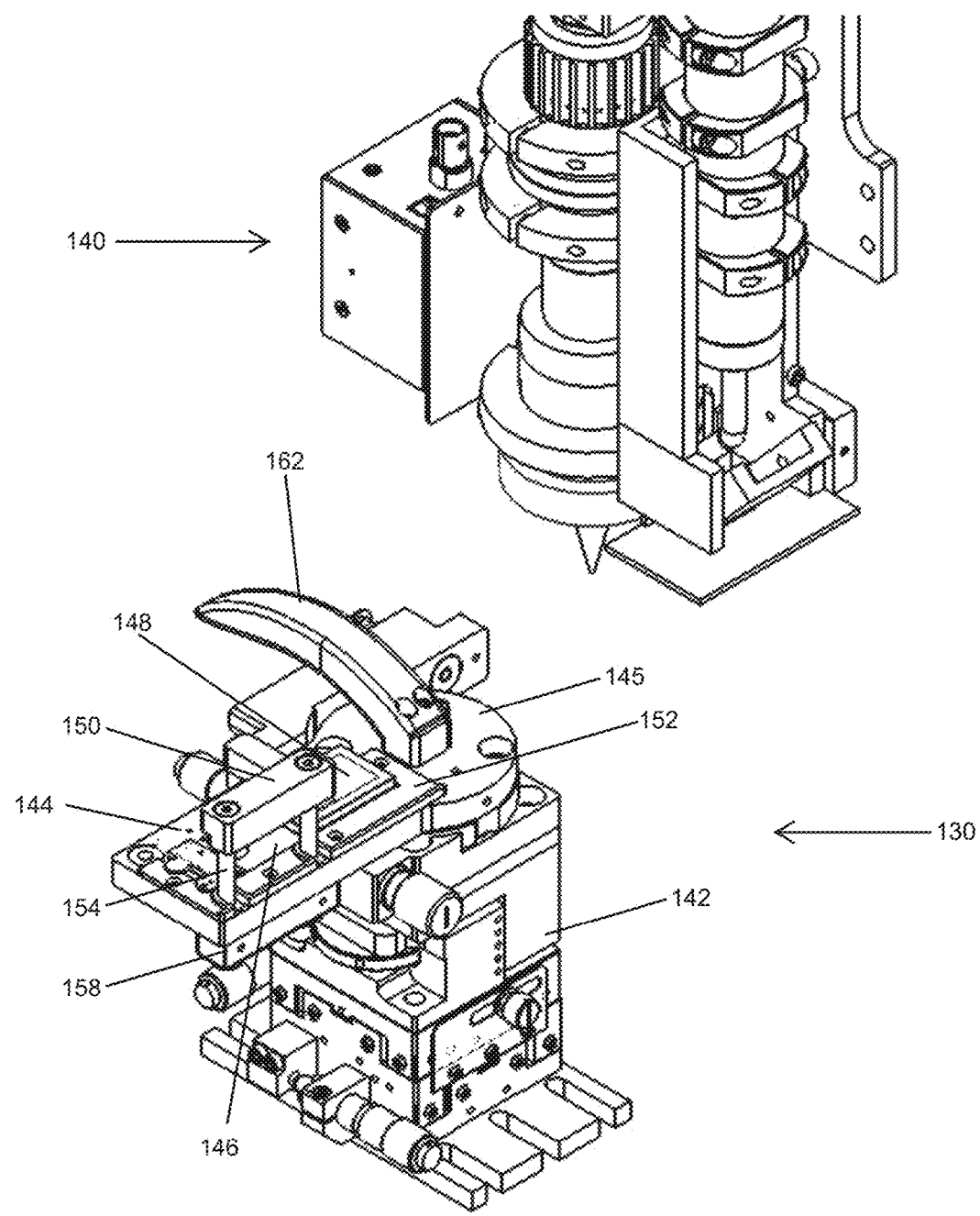
FIGS. 2A-2B depict an embodiment of a carousel for rotating lateral flow cells in a cartridge from a loading position (FIG. 2A) to an imaging position (FIG. 2B) under a microarray imaging system.

The following detailed description is presented to enable any person skilled in the art to make and use the invention. For purposes of explanation, specific nomenclature is set forth to provide a thorough understanding of the present application. However, it will be apparent to one skilled in the art that these specific details are not required to practice the invention. Description of specific embodiments and applications is provided only as representative examples. This description is an exemplification of the principles of the invention and is not intended to limit the invention to the particular embodiments illustrated.

This description is intended to be read in connection with the accompanying drawings, which are considered part of the entire written description of this invention. The drawing figures are not necessarily to scale and certain features of the invention may be shown exaggerated in scale or in somewhat schematic form in the interest of clarity and conciseness. In the description, relative terms such as "front," "back" "up," "down," "top" and "bottom," as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected" and "attached," refer to a relationship wherein structures are secured or attached to one another either directly or indirectly through intervening structures, as well as both movable or rigid attachments or relationships, unless expressly described otherwise.

As used herein, the term "sample" includes biological samples such as cell samples, bacterial samples, virus samples, samples of other microorganisms, samples obtained from a mammalian subject, preferably a human subject, such as tissue samples, cell culture samples, stool samples, and biological fluid samples (e.g., blood, plasma, serum, saliva, urine, cerebral or spinal fluid, lymph liquid and nipple aspirate), environmental samples, such as air samples, water samples, dust samples and soil samples.

The term "monolith," "monolith adsorbent" or "monolithic adsorbent material," as used in the embodiments described herein, refers to a porous, three-dimensional adsorbent material having a continuous interconnected pore structure in a single piece. A monolith is prepared, for example, by casting, sintering or polymerizing precursors into a mold of a desired shape. The term "monolith" is meant to be distinguished from two or more filters that are placed next to each other or pressed against each other. The term "monolith adsorbent" or "monolithic adsorbent material" is meant to be distinguished from a collection of individual adsorbent particles packed into a bed formation or embedded into a porous matrix, in which the end product comprises individual adsorbent particles. The term "monolith adsorbent" or "monolithic adsorbent material" is also meant to be distinguished from a collection of adsorbent fibers or fibers coated with an adsorbent, such as filter papers or filter papers coated with an adsorbent.

The term "specifically bind to" or "specific binding," as used in the embodiments described herein, refers to the binding of the adsorbent to an analyte (e.g., nucleic acids) with a specificity that is sufficient to differentiate the analyte from other components (e.g., proteins) or contaminants in a sample. In one embodiment, the term "specific binding" refers to the binding of the adsorbent to an analyte in a sample with a binding affinity that is at least 10-fold higher than the binding affinity between the adsorbent and other components in the sample. A person of ordinary skill in the art understands that stringency of the binding of the analyte to the monolith and elution from the monolith can be controlled by binding and elution buffer formulations. For example, elution stringencies for nucleic acids can be controlled by salt concentrations using KCl or NaCl. Nucleic acids, with their higher negative charge, are more resistant to elution than proteins. Temperature, pH, and mild detergent are other treatments that could be used for selective binding and elution. Thermal consistency of the binding and elution may be maintained with a heat block, water bath, infrared heating, and/or heated air directed at or in the solution. The manipulation of the binding buffer is preferable since the impact of the modified elution buffer on the downstream analyzer would need to be evaluated.

The term "nucleic acid," as used in the embodiments described herein, refers to individual nucleic acids and polymeric chains of nucleic acids, including DNA and RNA, whether naturally occurring or artificially synthesized (including analogs thereof), or modifications thereof, especially those modifications known to occur in nature, having any length. Examples of nucleic acid lengths that are in accord with the present invention include, without limitation, lengths suitable for PCR products (e.g., about 50 to 700 base pairs (bp)) and human genomic DNA (e.g., on an order from about kilobase pairs (Kb) to gigabase pairs (Gb)). Thus, it will be appreciated that the term "nucleic acid" encompasses single nucleotides as well as stretches of nucleotides, nucleosides, natural or artificial, and combinations thereof, in small fragments, e.g., expressed sequence tags or genetic fragments, as well as larger chains as exemplified by genomic material including individual genes and even whole chromosomes. The term "nucleic acid" also encompasses peptide nucleic acid (PNA) and locked nucleic acid (LNA) oligomers.

The term "hydrophilic surface" as used herein, refers to a surface that would form a contact angle of 45° or smaller with a drop of pure water resting on such a surface. The term "hydrophobic surface" as used herein, refers to a surface that would form a contact angle greater than 45° with a drop of pure water resting on such a surface. Contact angles can be measured using a contact angle goniometer.

Sample-to-Answer Sample Analysis System 100

A principal aspect of the instant application relates to an LFC positioning module 130 for a sample-to-answer sample analysis system 100. FIG. 1 is a diagram of an exemplary sample analysis system 100, which includes a sample processing module 110 containing a sample purification device, a temperature control module 120 containing a heating and cooling device, a detection module 140 containing a microarray imaging system, and an LFC positioning module 130 for positioning the LFCs into the field of view of the detection module 140 containing the microarray imaging system.

Sample Processing Module 110

The sample processing module 110 prepares a sample for analysis. Such preparation typically involves purification or isolation of the molecules of interest, such as DNA, RNA or protein, from the original sample using a sample purification device. The isolated molecules of interest are then transferred into the reaction chamber of an LFC. In some embodiments, the reaction chamber contains a microarray for detection of the molecules of interest and a hydrophilic interior surface to facilitate the complete filling of the reaction chamber with an aqueous liquid.

In some embodiments, the sample purification device includes a monolith that binds specifically to nucleic acids. In certain embodiments, the sample purification device is a pipette tip containing a filter that binds specifically to the molecules of interest. Exemplary filters are further described in in U.S. Pat. No. 7,785,869 and U.S. Pat. No. 8,574,923, both of which are incorporated by reference in their entirety.

In some other embodiments, the sample processing module 110 further comprises a cell lysis chamber having a plurality of cell lysis beads and a magnetic stirrer. Cell lysis is achieved by rotating the magnetic stirrer inside the cell lysis chamber in the presence of the cell lysis beads. The rotation of the magnetic stirrer is created by an alternating magnetic field induced by the rotation of north and south poles of a magnet, which is external to the tube. In some embodiments, the magnet is a cylinder shaped magnet. The magnet rotates about an axis A and causes a magnet stir element in the chamber to rotate in the same direction along an axis B that is parallel to axis A. The rotating magnetic stir element collides with beads, which lyse cells in the process. The magnet may be positioned alongside, above, below or diagonally from the chamber. In some embodiments, a cylinder shaped magnet is rotating about an axis that is parallel to a surface that the cell lysis chamber is placed on. The cell lysis beads can be any particle-like or bead-like material that has a hardness greater than the hardness of the cells to be lysed. The cell lysis beads may be made of plastic, glass, ceramics, or any other non-magnetic materials, such as non-magnetic metal beads. In certain embodiments, the cell lysis beads are rotationally symmetric to one axis (e.g., spherical, rounded, oval, elliptic, egg-shaped, and droplet-shaped particles). In other embodiments, the cell lysis beads have polyhedron shapes. In other embodiments, the cell lysis beads are irregular shaped particles. In yet other embodiments, the cell lysis beads are particles with protrusions. The magnetic stirrer can be a bar-shaped, cross-shaped, V-shaped, triangular, rectangular, rod or disk-shaped stir element, among others. In some embodiments, the magnetic stirring element has a rectangular shape. In some embodiments, the magnetic stirrer has a two-pronged tuning fork shape. In some embodiments, the magnetic stirrer has a V-like shape. In some embodiments, the magnetic stirrer has a trapezoidal shape. In certain embodiments, the longest dimension of the stir element is slightly smaller than the diameter of the container (e.g. about 75-95% of the diameter of the container). In certain embodiments, the magnetic stirrer is coated with a chemically inert material, such as polymer, glass, or ceramic (e.g., porcelain). In certain embodiments, the polymer is a biocompatible polymer such as PTFE and parylene. A more detailed description of the magnetic lysis method is described in application Ser. No. 12/886,201, which is hereby incorporate by reference.

Temperature Control Module 120

The temperature control module 120 controls the temperature of the reaction chamber during amplification and/or binding reactions. In certain embodiments, the temperature control module comprises a heating and cooling device with a flexible temperature control surface, as described in U.S. Pat. Nos. 7,955,840 and 7,955,841, both of which are hereby incorporated by reference in their entirety. In other embodiments, the temperature control module 120 employs a heating and cooling device with a hard, flat temperature control surface as described in U.S. patent application Ser. No. 14/743,389, filed Jun. 18, 2015, the teachings of which are expressly incorporated by reference herein.

In some embodiments, the temperature control module 120 includes a thermoelectric device. One or more thermoelectric devices can be integrated into the module. In other embodiments, the temperature control module 120 further comprises a temperature sensor. Examples of temperature sensors are resistance thermal devices (RTDs), thermocouples, thermopiles, and thermistors.

In some embodiments, the thermoelectric device is a Peltier device made of ceramic materials. Examples of ceramic materials include: alumina, beryllium oxide, and aluminum nitride.

In other embodiments, the thermoelectric device is a thin film semiconductor (e.g, bismuth telluride). In other embodiments, the thermoelectric device is a thermoelectric couple made of p and n type semiconductors. Examples of p and n type semiconductors are bismuth antimony, bismuth telluride, lead telluride, and silicon germanium.

In some embodiments, the thermoelectric device has a heat sink coupled to one side and a heat spreader coupled to the other side. Examples of heat sinks and heat spreaders are copper, aluminum, nickel, heat pipes, and/or vapor chambers. During operation, the heat spreader makes intimate contact with an exterior surface of the reaction chamber and controls the temperature inside the reaction chamber. In some embodiments, the heat sink and/or heat spreader are coupled to the thermoelectric device with thermally-conductive epoxy, thermally-conductive adhesives, liquid metal (e.g., gallium) or solder (e.g., indium). In some embodiments, the temperature control module 120 further comprises a fan under the heat sink. In one embodiment the heat spreader is flat. In some of these embodiments the heat spreader is rectangular with dimensions that range from 3 mm×3 mm to 20 mm×20 mm. The thickness of the heat spreader is preferably 0.05 to 5 mm, and more preferably 0.1 to 0.5 mm, and even more preferably 0.15 to 0.3 mm.

LFC Positioning Module 130

The LFC positioning module 130 positions the LFC for detection of signals in the microarray by the detection module 140. In one aspect, the LFC positioning module includes (1) a carousel comprising a platform and a sample loading tray mounted on the platform, and (2) a stage comprising a positioning system for positioning the carousel. The sample loading tray is configured for holding a cartridge comprising one or more LFCs. In some embodiments, the carousel is movable relative to the stage. In some embodiments, the LFC positioning module 130 is configured to allow heating and cooling of LFCs in the sample loading tray by the temperature control module 120, and real time monitoring of a reaction in the reaction chamber of a LFC by the detection module 140. In other embodiments, the carousel is rotatable e relative to the stage. In other embodiments, the carousel is capable of spinning to remove liquid from a reaction chamber of an LFC.

In other embodiments, the carousel further comprises a clamp having a top bar, a bottom bar and at least one supporting rod connecting the top bar and the bottom bar. The platform and the sample loading tray are disposed between the top bar and the bottom bar of the clamp. The clamp is movable relative to the platform and is capable of immobilizing a cartridge in the sample loading tray when the clamp is moved to a locked position.

In other embodiments, the positioning module 130 contains a built-in heating and cooling device that is capable of heating and cooling the LFC(s) in the cartridge. In other embodiments, the carousel is movable to a reaction position to bring the cartridge into contact with a heating and cooling device to facilitate reactions in the reaction chamber of an LFC within the cartridge. In some embodiments, the heating and cooling device is configured to allow real-time monitoring of a reaction within the reaction chamber of the LFC by the detection module 140.

In certain embodiments, the stage includes a motor-driven rotor connected to the carousel to facilitate its rotation. Rotation of the carousel sets in rotational motion a cartridge containing an LFC. This centrifugal force drives the water droplets within reaction chambers toward an absorbent, leaving the reaction chamber in a dry state. Thus, microarray elements, including bound and/or amplified probes are retained in a dry state. Following the drying procedure, the rotational velocity of the carousel decreases and enters an indexing mode for imaging. During this mode, each of the reaction chambers indexes into position under a microarray imaging camera. An image is acquired, processed and analyzed. Then, the test result is reported.

Figure 2B:
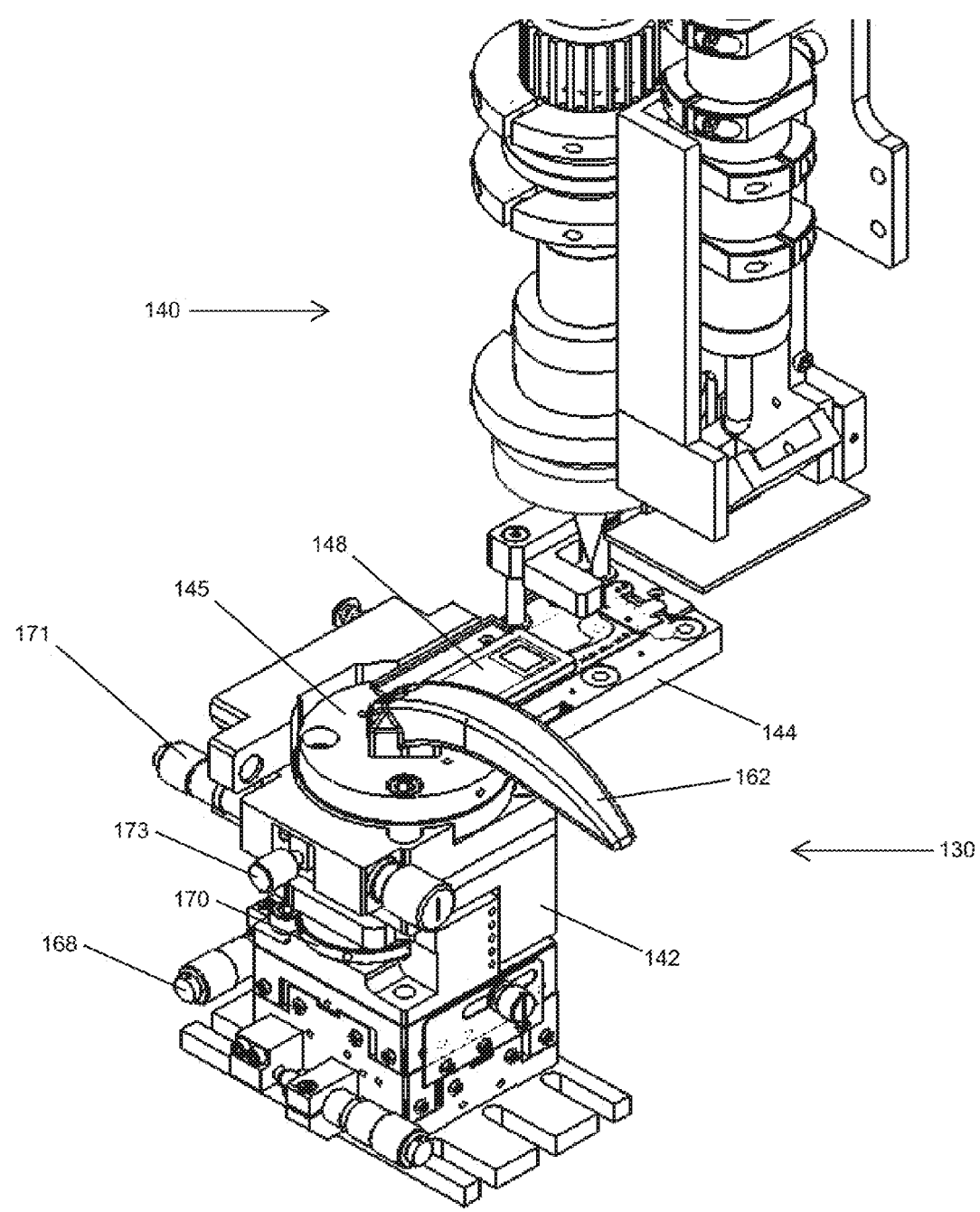

In an embodiment shown in FIGS. 2A-2B, the LFC positioning module 130 includes a stage 142 and a rotatable carousel 144. The rotatable carousel 144 comprises a platform 145 with a sample loading tray 152 that holds a cartridge 146 comprising a single LFC. The carousel 144 is connectively linked to a clamp 150 that immobilizes the cartridge 146 in the sample loading tray 152 in a locked position, and allows the removal of the cartridge 146 from the sample loading tray 152 or insertion of the cartridge 146 into the sample loading tray 152 in an open position. In this embodiment, the clamp 150 contains two supporting rods 154 connected to a top bar 156 and bottom bar 158 as part of the platform 145. The outwardly extending handle 162 is attached to the platform 145 to facilitate rotation or indexing of the carousel 144 from a loading position (FIG. 2A) to an imaging position (FIG. 2B).

Figure 3A:
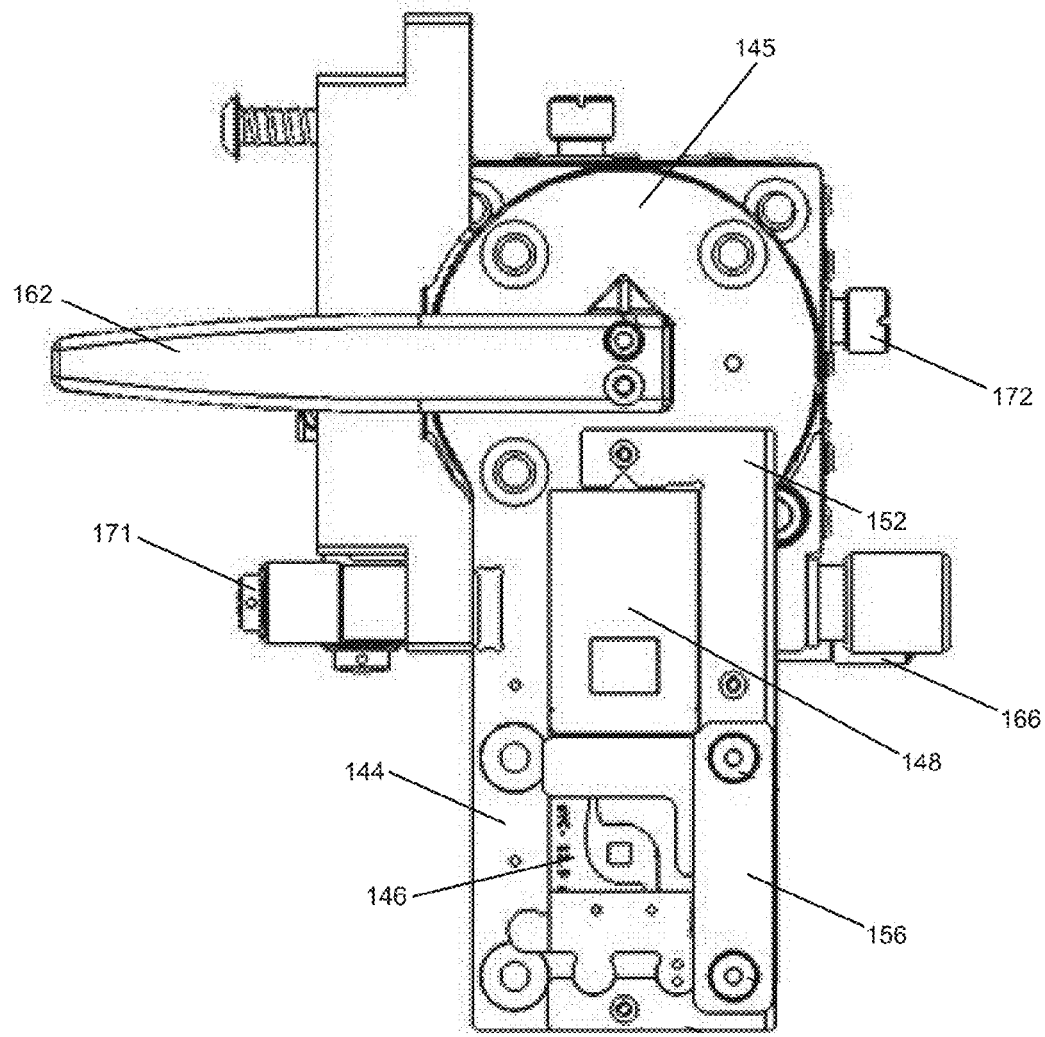
FIGS. 3A and 3B show the top view (FIG. 3A) and bottom view (FIG. 3B) of the carousel, including the clamp, in FIGS. 2A-2C.
Figure 3B:
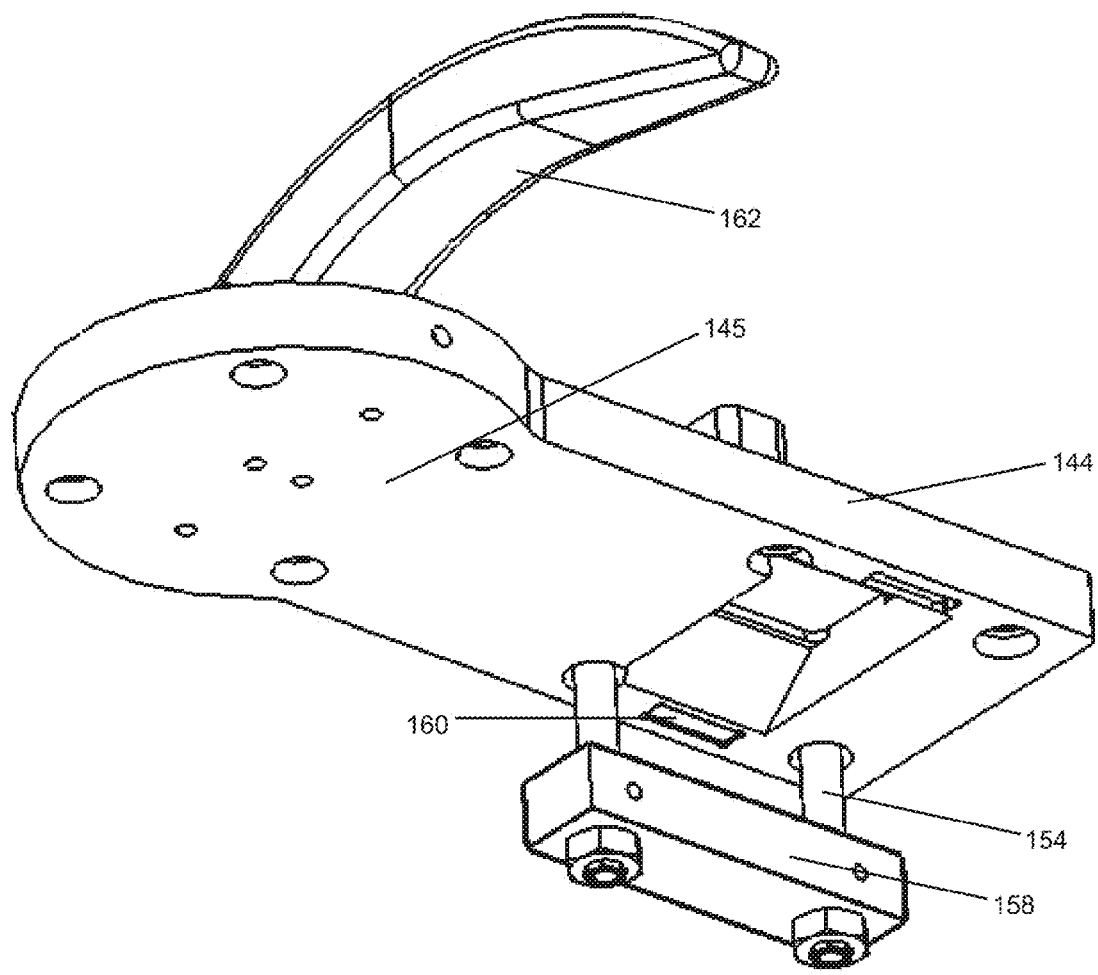

FIG. 3A is a top view of the carousel 144, showing the platform 145, a handle 162, the sample loading tray 152, the cartridge 146 and the top bar 156 of the clamp 150. FIG. 3B is a bottom view of the carousel 144, including the bottom bar 158 and the supporting rods 154. The sample tray 152 resides in the carousel 144 between the top and bottom bars 156, 158. The sample loading tray 152 remains in a fixed position while the clamp 150 translocates up or down, locking the cartridge 146 in the sample loading tray 152 at the down position (locked position) and allowing the cartridge 146 to be inserted into, or removed from, the sample loading tray 152 at the up position (open position). A magnet 160 may be placed at the bottom side of the platform 145 for releasable attachment to the bottom bar 158 to keep the clamp 150 at an open position.

In some embodiments, a motor-driven rotor (not shown) is disposed within the stage 142 for rotating the carousel 144 holding the disposable cartridge 146. The rotor rotates the carousel 144 and cartridge 146 at rotational velocities producing centrifugal forces sufficient to drive water droplets from reaction chambers in the LFCs 148 toward an absorbent 62 in a waste chamber 60 therein (FIG. 10A), drying the LFC 148 so as to enhance the imaging of nucleic acids or proteins bound to microarrays in the LFCs 148. Exemplary motors for rotating the carousel 144 include a stepper motor, a servo motor and a DC motor. In one embodiment the rotor rotates the carousel at rotational velocities of at least 200 rpm, at least 300 rpm, at least 500 rpm, at least 1000 rpm; between about 200 to 5000 rpm, between 200 to 2500 rpm, between 250 to 1000 rpm, or between 400 to 800 rpm.

Upon completion of the drying process, the rotational velocity of the carousel 144/cartridge 146 decreases, whereupon the drying/positioning module enters an indexing mode for imaging. During this mode, each of the microarrays is indexed into position under a microarray imaging camera in the detection module 140. Specifically, the carousel 144 is indexed into position so that a desired microarray enters the field of view for imaging. Images of biomolecule binding results are acquired, processed, analyzed and reported.

In some embodiments, including FIGS. 2A-2B, the stage 142 includes an "XYZ positioner system" comprising knobs 166, 168, 170 for positioning the LFCs in appropriate positions for imaging. Actuating the knobs 166, 168, 170 enables the user to vary the position of the microarrays in the x, y, z axes for imaging bound biomolecules in the reaction chamber 10 and/or microarrays 40 therein (see e.g., FIG. 10A). Additionally, in some embodiments, an angular adjustment micrometer 171 is employed to adjust the tilt or yaw angle of the platform 145. Once the sample tray is properly located under the camera for imaging, the positions of the X and Y stages are locked in place, for example by set screws such as the Y stage locking screw 172 depicted in FIG. 2B. In some embodiments, a platform locking screw 173 prevents rotation of the platform 145 when in the imaging position.

Figure 4A:
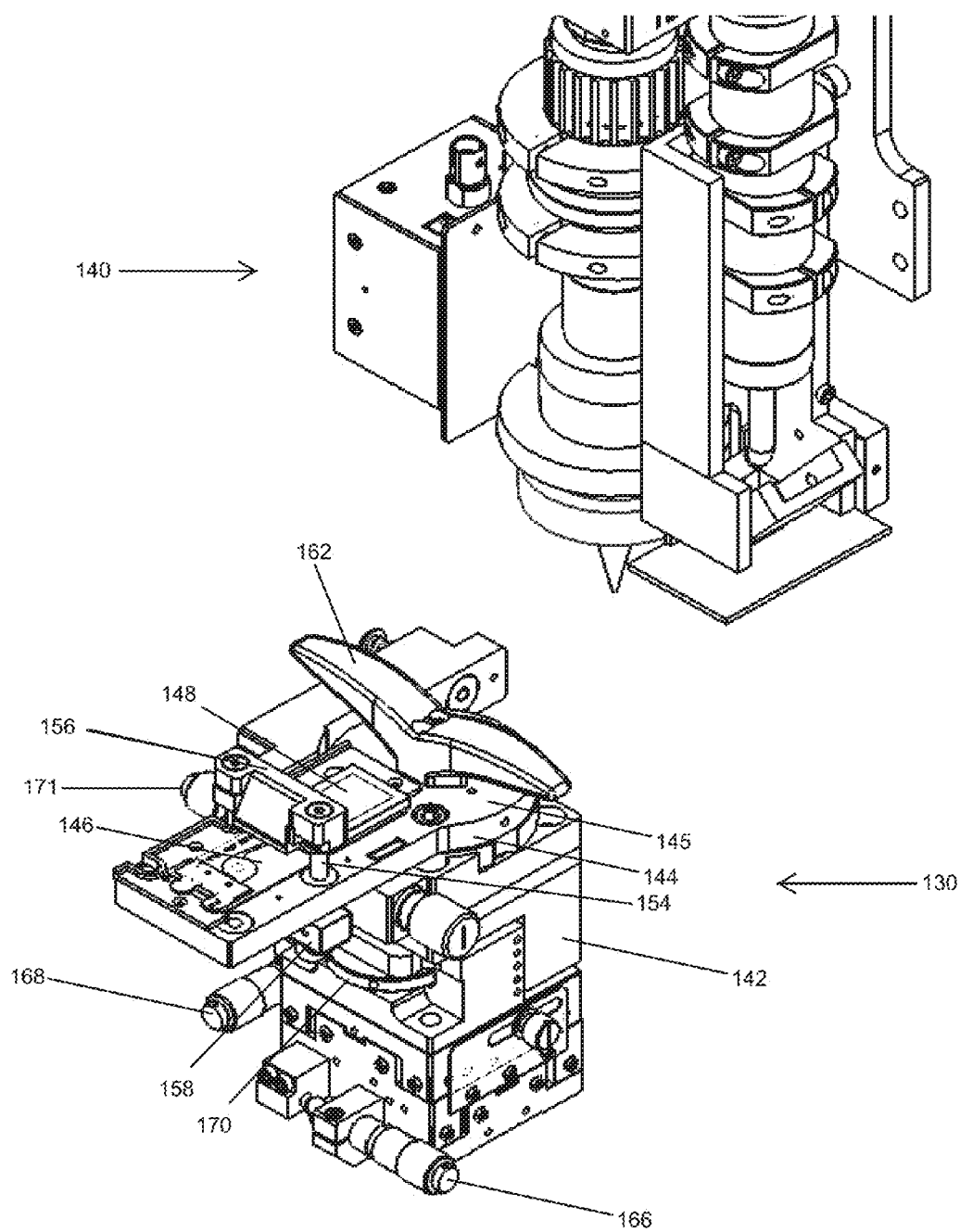
FIGS. 4A-4B depict another embodiment of a carousel for rotating LFCs in a cartridge from a loading position (FIG. 4A) to an imaging position (FIG. 4B) under a microarray imaging system.
Figure 4B:
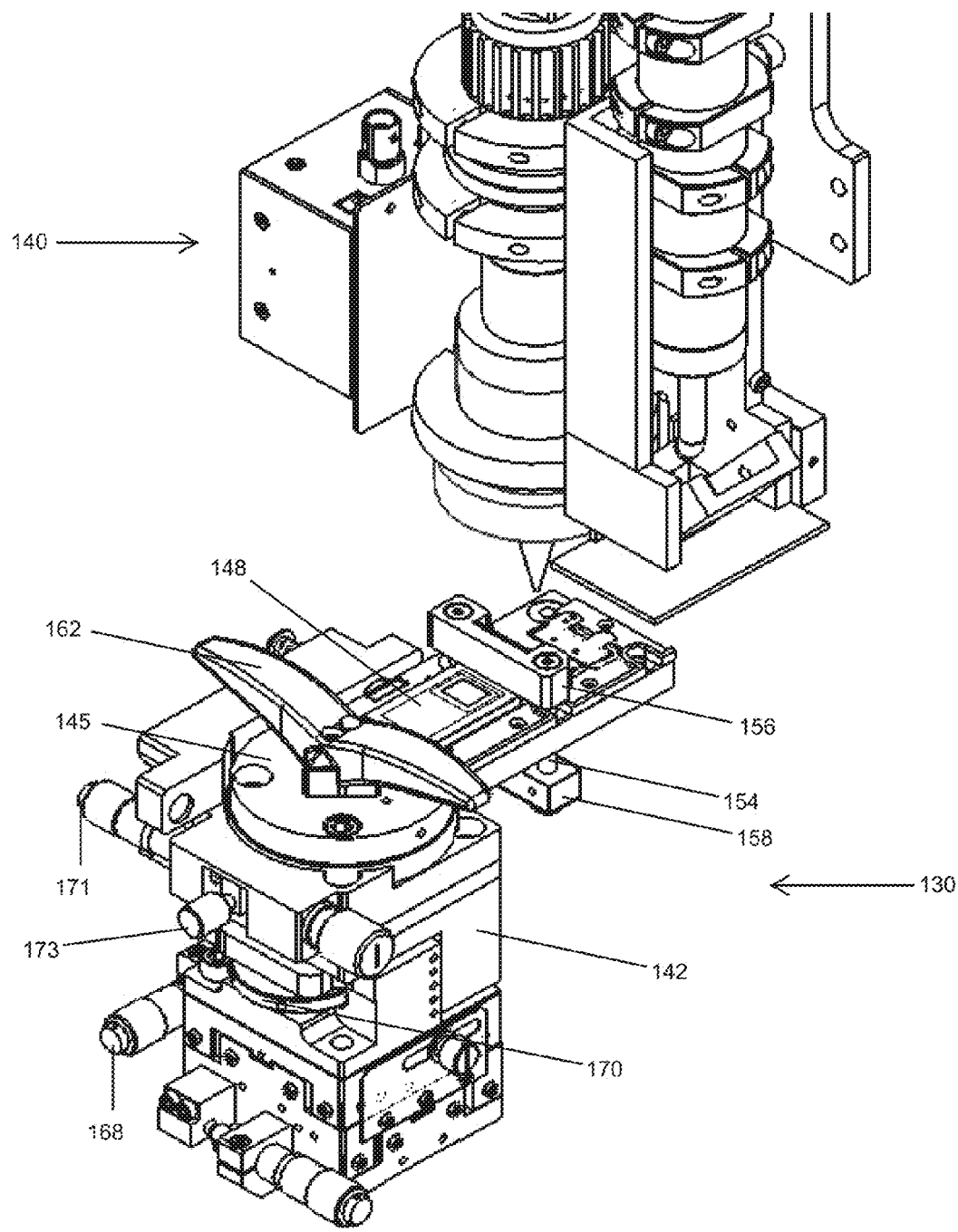

FIGS. 4A-4B depict another embodiment of a carousel 144 for rotating LFCs in a cartridge from a loading position (FIG. 4A) to an imaging position (FIG. 4B) under a microarray imaging system.

Figure 5:
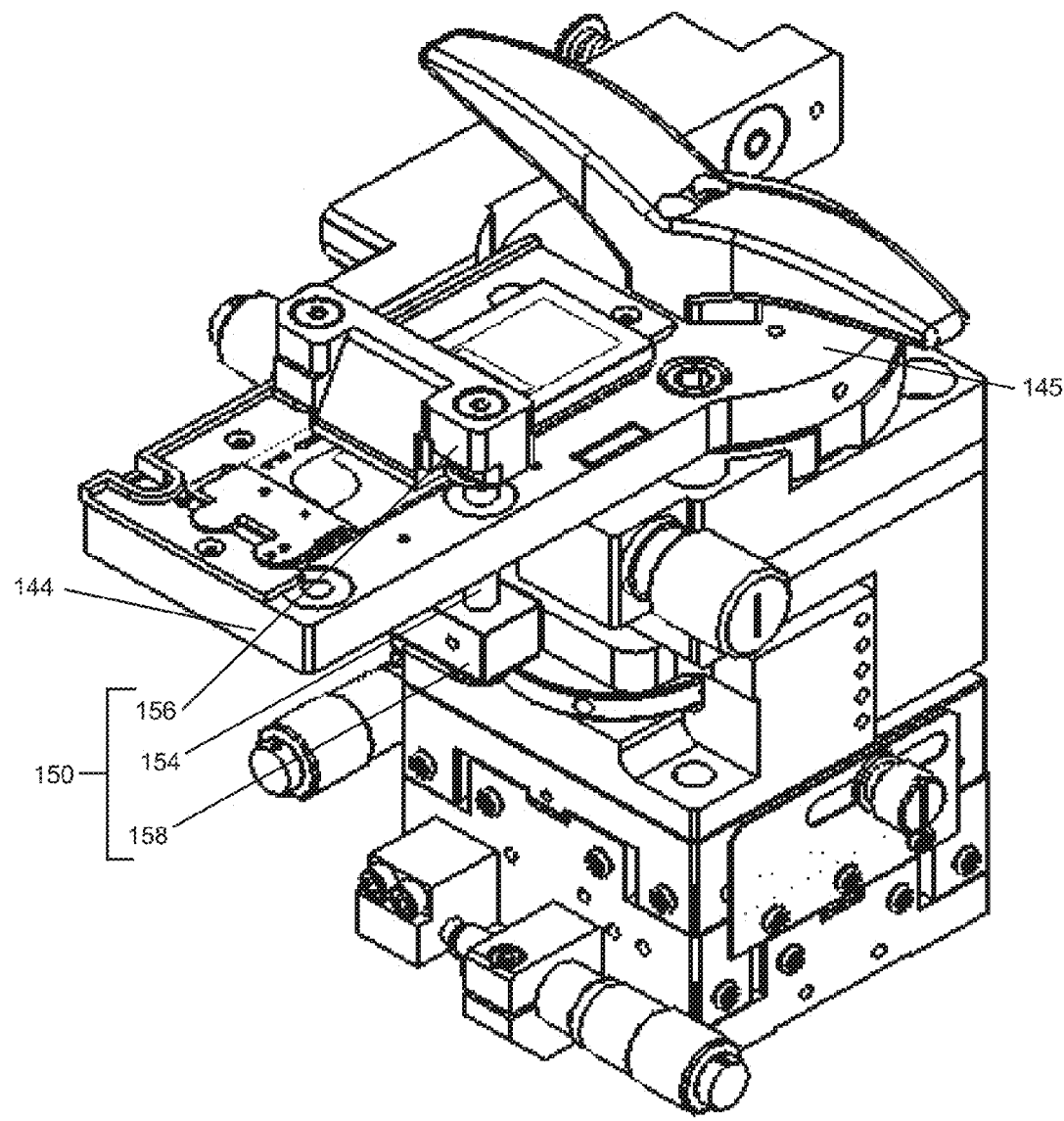
FIG. 5 depict another embodiment of a carousel for rotating LFCs in a loading position.
Figure 6:
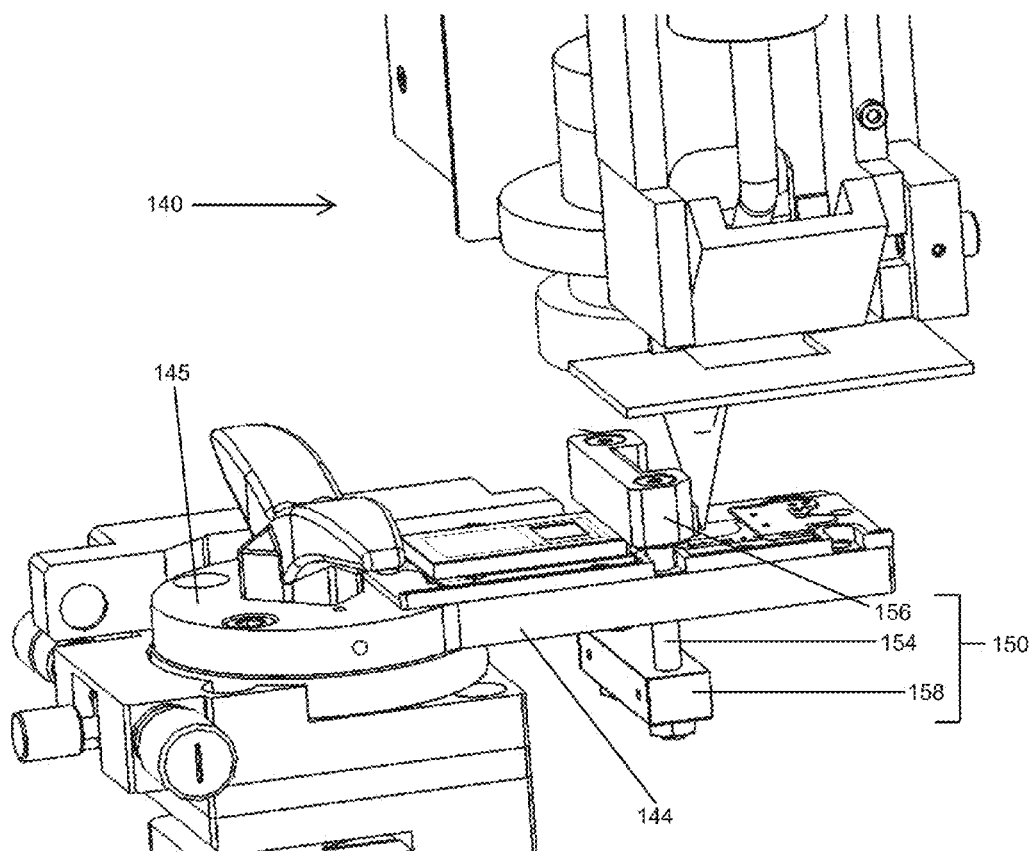
FIG. 6 depicts the embodiment of a carousel for rotating LFCs of FIG. 5 in an imaging position under a microarray imaging system.

FIGS. 5 and 6 depict another embodiment of a carousel for rotating LFCs in a cartridge from a loading position (FIG. 5) to an imaging position (FIG. 6) under a microarray imaging system.

Figure 7:
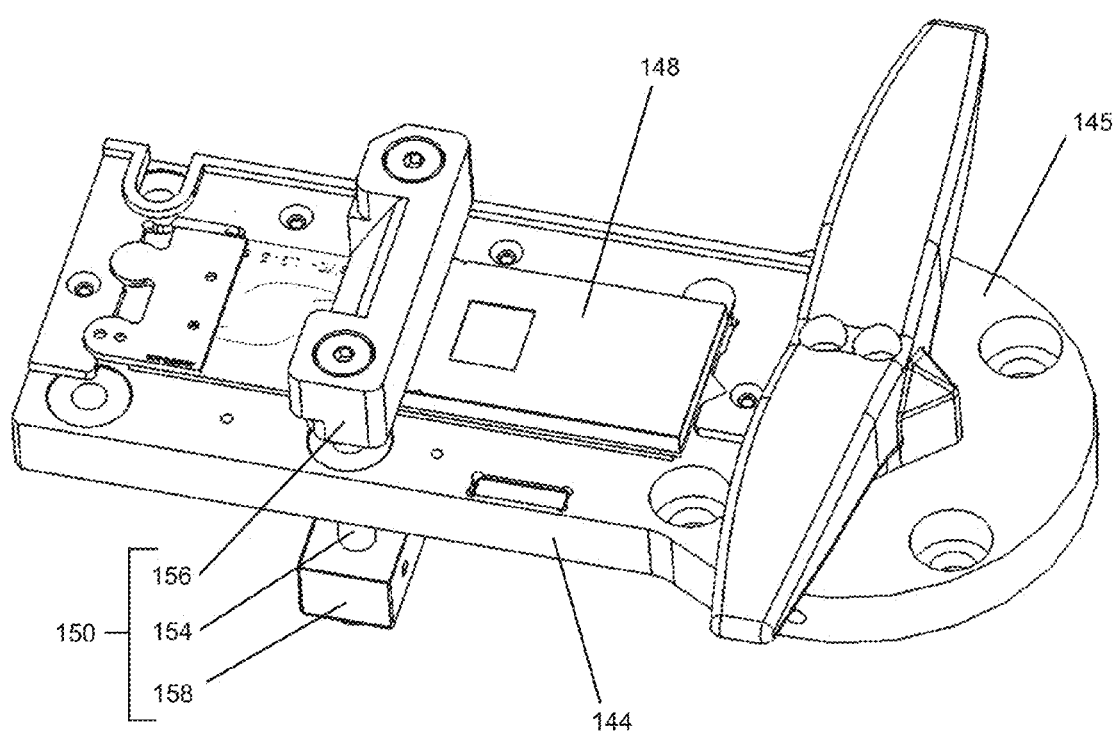
FIG. 7 show the carousel in FIGS. 5 and 6.

FIG. 7 show the carousel 144 in FIGS. 5 and 6.

Figure 8:
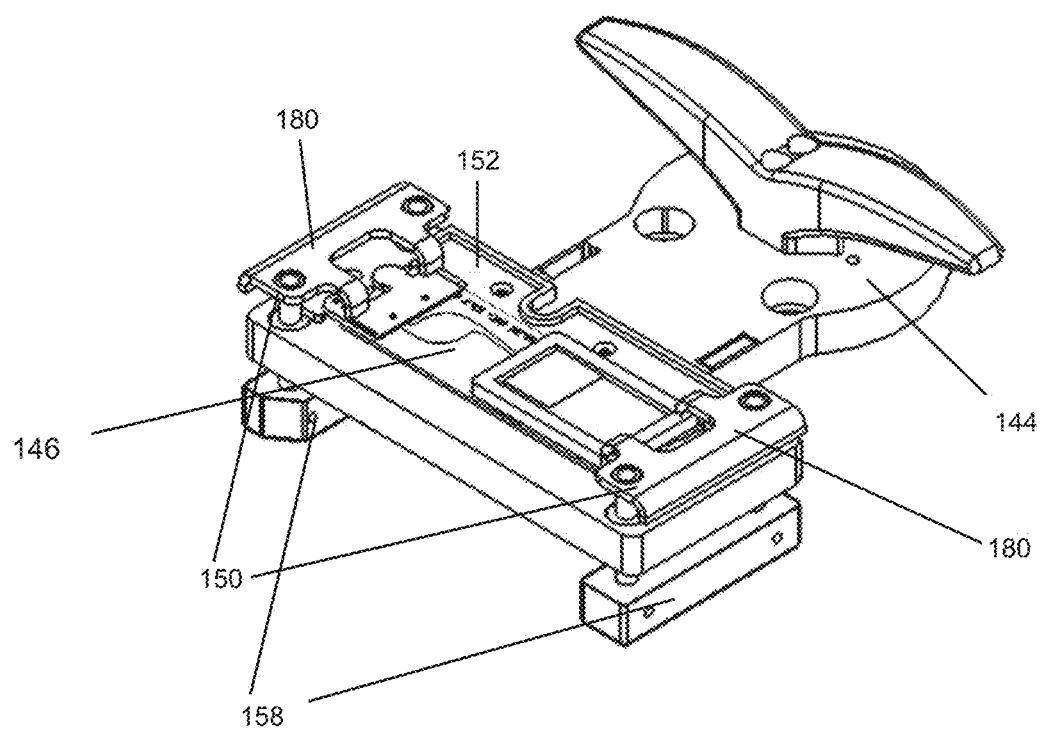
FIG. 8 shows the top of another carousel embodiment, including dual clamps for positioning a microarray in the field of view of an imager.
Figure 9A:
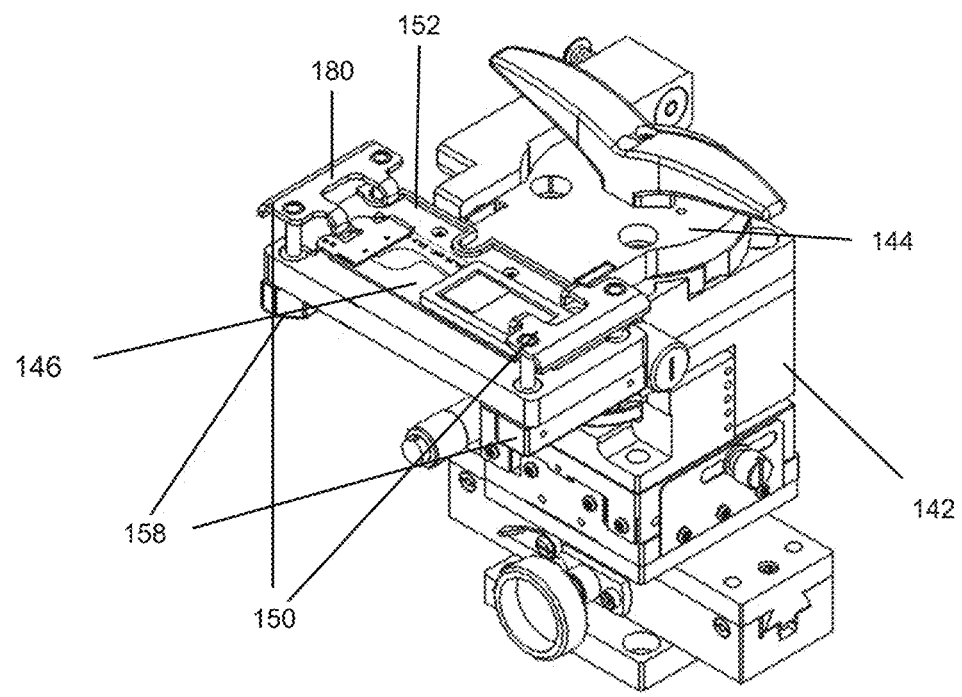
FIGS. 9A-9B depict an embodiment of a positioning module for imaging microarrays comprising the carousel of FIG. 8 for rotating a sample cartridge from a loading position (FIG. 9A) to a position for imaging (FIG. 9B).
Figure 9B:
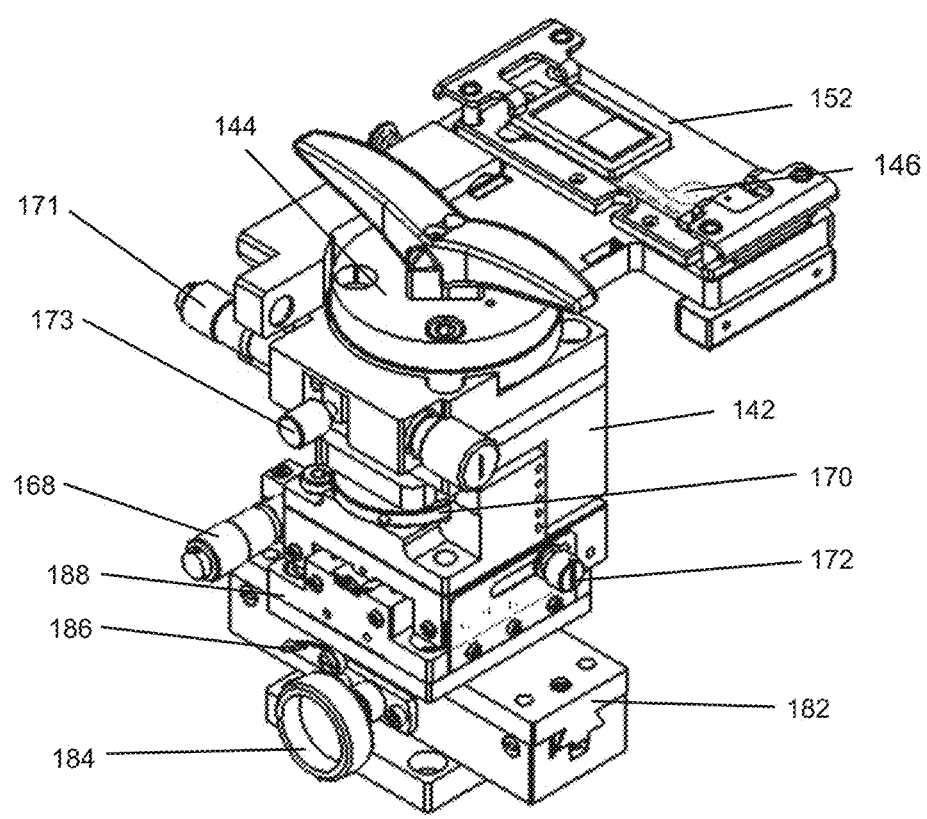

FIGS. 8 and 9A-9B show an embodiment of a positioning module for microarray imaging comprising a stage 142 and a rotatable carousel 144. It is understood that different elements of each embodiment of the microarray imaging positioning module can be used interchangeably as practicably allowed.

FIG. 8 shows the carousel 144 with the attached sample loading tray 152. The sample loading tray 152 has two independent clamp 150 that can be slide up and down the Z axis. The clamps 150 each contains a top bar or bracket 180 and a bottom bar 158. When the clamp 150 is in a lifted position, the bottom bar 158 is held in place by a magnetic latch to facilitate sample loading with the same mechanism as shown in FIG. 3B. The sample loading tray 152 can be used with cartridges 146 comprising different formats of microarray packaging—from standard 1"×3" glass or plastic substrates with microarrays printed on them to microarrays encapsulated into a microfluidic flow cell that may have complex thickness profiles due to such features as sealable inlet port and/or integral waste chambers. Non-limiting examples of LFC 148 and cartridge 146 are depicted in FIGS. 10 and 11. Because of their low-profile design, the clamping brackets do not block the excitation beam propagating at an oblique angle, which virtually eliminates restrictions on the position of microarray on the substrate. In some embodiments, the low profile design allows an oblique angle of view from the vertical of the microarray on the substrate of at least about 70 degrees. In other embodiments, the angle of view is at least about 75, 80 or 85 degrees. In still other embodiments, the angle of view is at least about 87.5 degrees.

FIGS. 9A-B show a positioning device for microarray imaging comprising a stage 142 and a rotatable carousel 144 with the carousel in the sample loading and imaging positions. In FIG. 9A, the carousel 144 is turned so that the sample loading tray 152 is in the sample loading position with the clamps 150 lifted and the magnetic latches engaged with the bottom bar 158. Once the sample cartridge 146 is loaded, the magnets are disengaged with the bottom bar 158 by pushing the top bar or bracket 180 of the clamp 150 down. The weight of the top bar or bracket 180 and the bottom bar 158 holds the clamp 150 down to secure the sample cartridge 146 in place.

FIG. 9B shows the controls in one embodiment of a stage 142 of a positioning device for microarray imaging, with the sample loading tray 152 moved into the imaging position. In some embodiments, the carousel 144 is locked with the sample loading tray 152 in the imaging position using a locking screw 173. The fine location of the microarray within the sample cartridge 146 when the sample loading tray 152 is in the imaging position both by an angular adjustment micrometer 171, which adjusts the angle of the rotary table comprising the carousel 144 and the sample loading tray 152 elements, as well as X, Y and Z axis controls incorporated into the stage 142. In this embodiment, the stage 142 comprises an X axis translation stage 182 for sample positioning along the X axis and an X axis positioning knob 184 for adjusting the movement and an X axis lock 186 for fixing the position of the X axis stage 182, allowing stable reproducible operation of the instrument's imaging system. In some embodiments, the X axis translation stage 182 comprises a rack-and-pinion mechanism for movement. In other embodiments, the X axis translation stage 182 comprises a worm gear or other suitable mechanism for movement. Also, in some embodiments, the X axis lock 186 comprises a lever mechanism that, when actuated, prevents the turning of the X axis positioning knob 184. In other embodiments, the X axis lock 186 comprises a set screw mechanism that, when engaged, contacts with and prevents the movement of the X axis translation stage 182. In some embodiments, the X axis translation stage 182 has a range of motion of at least 25 mm in each direction from center. In other embodiments, the X axis translation stage 182 has a range of motion of at least 30 or 35 mm in each direction from center. In still other embodiments, the X axis translation stage 182 has a range of motion of at least 40 mm in each direction from center.

FIG. 9B further depicts the stage 142 of this embodiment of a microarray imagery positioning device comprises a Y axis translation stage 188 for sample positioning along the Y axis and a Y axis positioning knob 168 for adjusting the movement and a Y axis lock 172 for fixing the position of the Y axis translation stage 188. In some embodiments, the Y axis translation stage 188 comprises a rack- and pinion mechanism for movement. In other embodiments, the Y axis translation stage 188 comprises a worm gear or other suitable mechanism for movement. In some embodiments, the Y axis lock 172 comprises a set screw mechanism that, when engaged, contacts with and prevents the movement of the Y axis translation stage 188. In some embodiments, the Y axis translation stage 188 has a range of motion of at least 5 mm in each direction from center. In other embodiments, the Y axis translation stage 188 has a range of motion of at least 10, 15 or 20 mm in each direction from center. In still other embodiments, the Y axis translation stage 188 has a range of motion of at least 25 mm in each direction from center.

Also shown in FIG. 9B, the stage also comprises a mechanism for Z axis control 170, in order to focus the microarray under the imaging device. In some embodiments, the Z axis control 170 is a thumbwheel. In other embodiments, the Z axis control 170 is a lever or other suitable mechanism for fine-scale adjustment of the Z axis for proper focus.

In some embodiments, the positioning device for microarray imaging embodiment shown in FIGS. 9A-9B is a component of a microarray imaging system further comprising an imaging device. In some further embodiments the imaging device is a camera.

In some embodiments the array imaging system further comprises an excitation energy source. The excitation energy source is focused on the microarray being imaged by the imaging device. In some further embodiments, the excitation energy source is tunable for the wavelengths emitted. In other further embodiments, the excitation energy source emits multiple wavelengths simultaneously. In some embodiments, the excitation energy strikes the array at an oblique angle. In some embodiments, the array imaging system is enclosed in a light-tight enclosure. In some embodiments, the array imaging system is sized to fit on the top of a lab bench along with a computer for data analysis.

In some embodiments, the sample cartridge comprises a microarray immobilized to a glass slide. In other embodiments, the sample cartridge comprises a microarray immobilized to a polymer-based slide. In some embodiments, the microarray is printed onto the glass or polymer-based slide. In some embodiments, multiple microarrays are immobilized to or printed onto the glass or polymer-based slide. In other embodiments, each microarray is enclosed within an LFC.

Figure 10A:
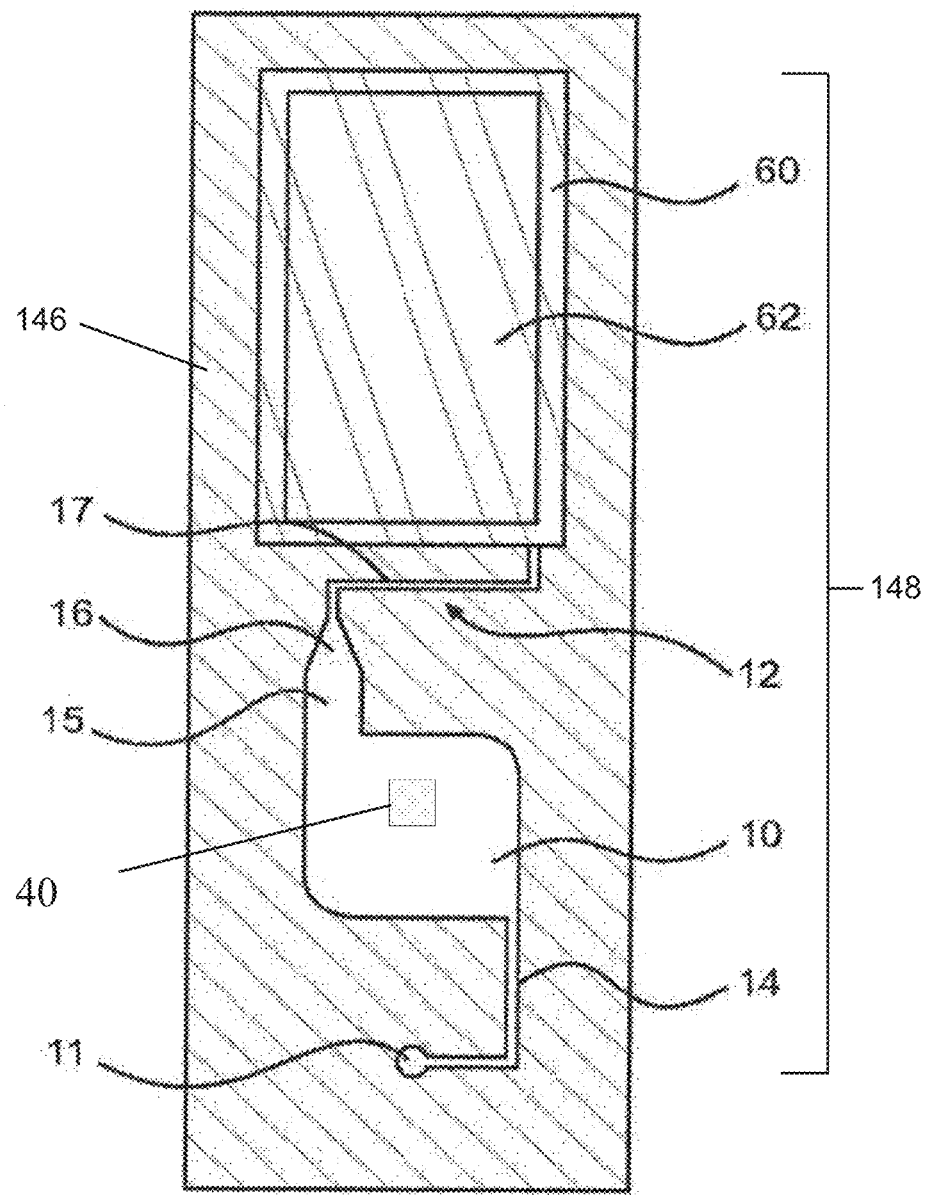
FIGS. 10A-10C show exemplary designs of LFC.
Figure 10B:
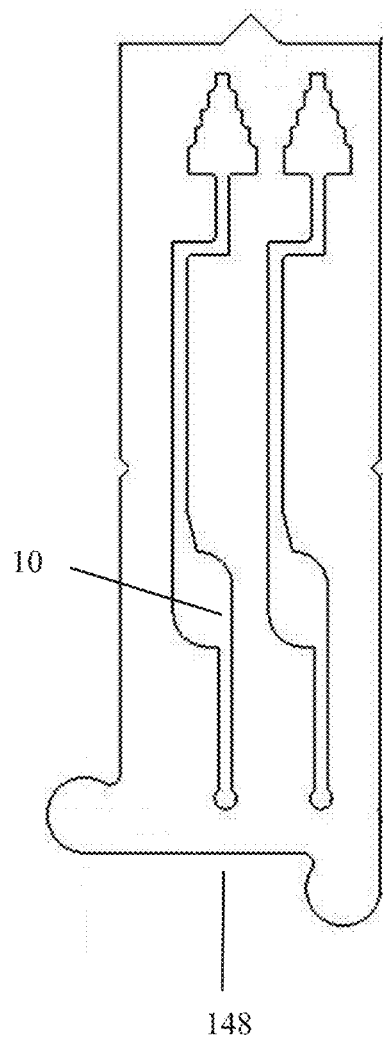
Figure 10C:
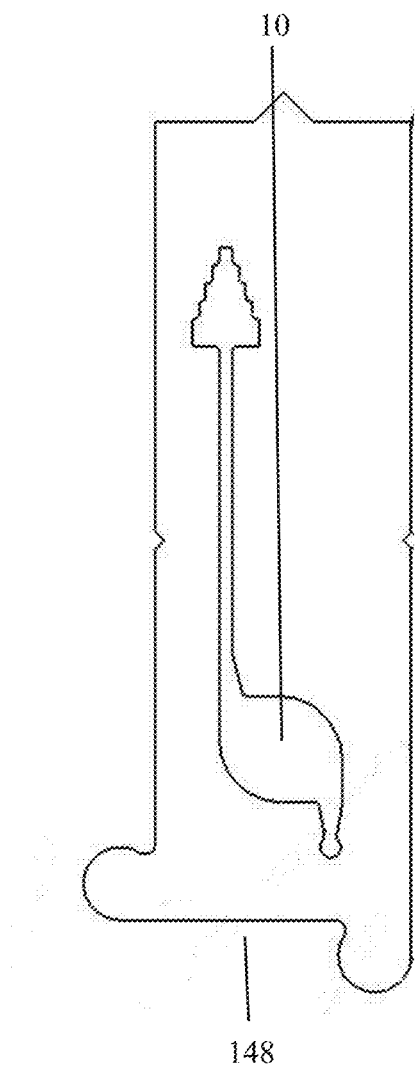

In some embodiments, the cartridge 146 contains a single LFC 148. FIG. 10A depicts an exemplary LFC 148. The LFC 148 comprises a reaction chamber 10, a waste chamber 60 and a channel 12 connecting the reaction chamber 10 to the waste chamber 60. The reaction chamber contains a microarray 40. The microarray 40 contains a plurality of attached probes for detection of nucleic acids or proteins. In some embodiments, the waste chamber 60 includes a liquid-retaining absorbent 62. Two additional LFC designs are shown in FIGS. 10B and 10C.

The microarray 40 can be a polynucleotide array or a protein/peptide array. In one embodiment, the microarray 40 is formed by printing gel spots as described in e.g., U.S. Pat. Nos. 5,741,700, 5,770,721, 5,981,734, 6,656,725 and U.S. patent application Ser. Nos. 10/068,474, 11/425,667 and 11/550,730, all of which are hereby incorporated by reference in their entirety.

The reaction chamber 10 has a plurality of interior surfaces including a bottom surface on which the microarray 40 is formed and a top surface that faces the bottom surface and is generally parallel to the bottom surface. In some embodiments, at least one of the plurality of interior surfaces is a hydrophilic surface that facilitate the complete filling of the reaction chamber 10. In one embodiment, the top surface of the reaction chamber 10 is a hydrophilic surface. Exemplary flow cell devices and embodiments are described in U.S. Pat. Nos. 8,680,025 and 8,680,026, which are expressly incorporated by reference in their entirety.

Figure 11C:
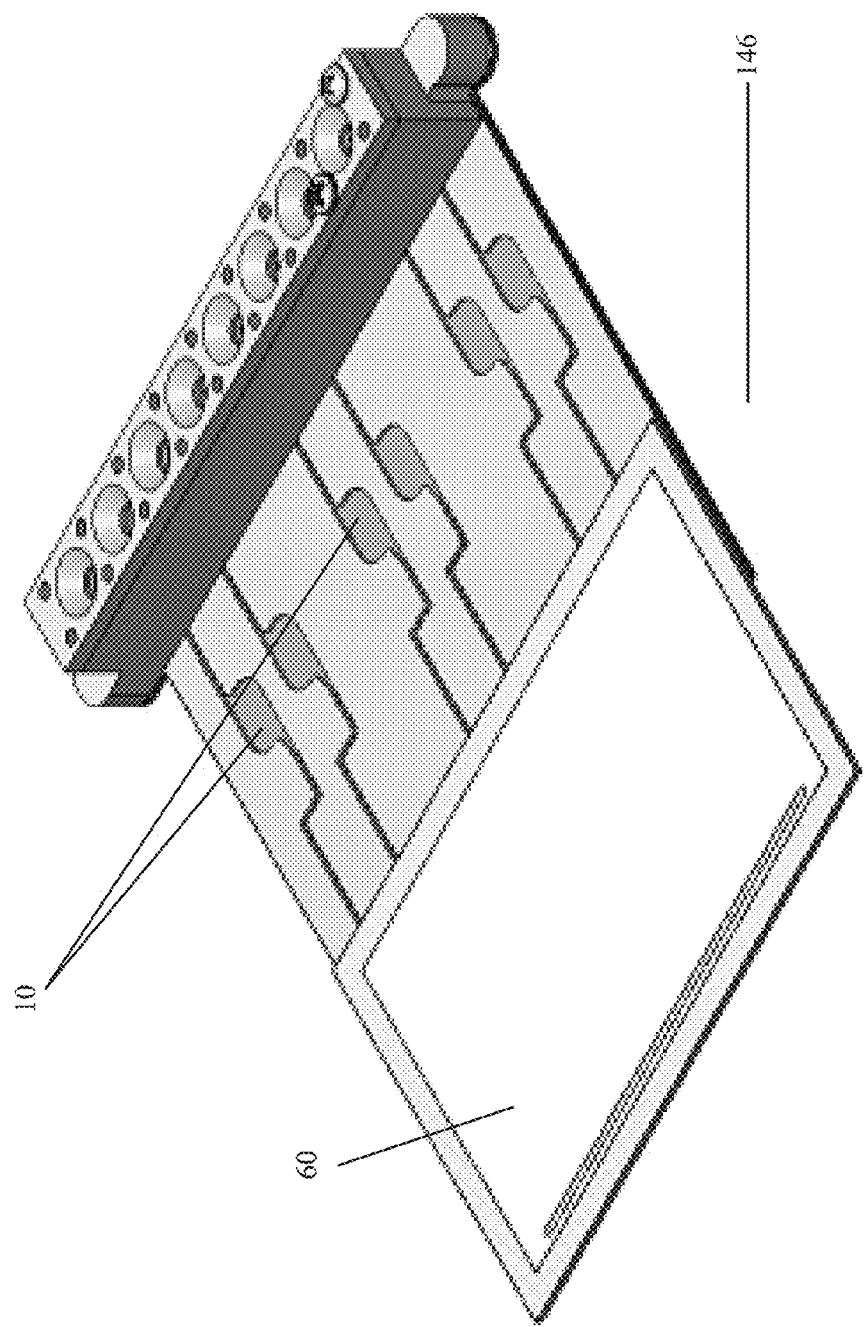

In other embodiments, the cartridge 146 contains LFCs 148. The cartridge 146 may contain one or more LFCs 148. In some embodiments, the cartridge 146 contains a unitary multi-microarray strip containing between 2 to 16 LFCs, between 4 to 12 LFCs or between 6-10 LFCs. In certain embodiments, the LFCs are shaped like wedges. FIG. 11A depicts a cartridge 146 with eight LFCs 148. The cartridge 146 is attached to a manifold 1100 (FIG. 11B) that controls liquid flow within the LFCs 148. Each LFC 148 contains a reaction chamber 1020 and each reaction chamber 1020 contains a microarray 1010. The reaction chambers 1020 are configured for allowing reagents, such as PCR reagents to interact with the microarrays 1010. By way of example, the manifold 1100 may direct reagents (e.g., PCR mixtures) pipetted in from a microtiter plate to the LFC 148 through dome valves 1120, which also act as a seal during thermal cycling preventing any leakage, and pin valves 1130, which are controlled by a linear actuator that enables them to be opened and closed. In an open position, the pin valves 1130 allow liquid flow during the wash steps. In a closed position, the pin valves 1130 help trap the reagents in the reaction chamber 1010 of the LFC 148 during e.g., thermal cycling. The absorbent 1140 attached to the manifold 1100 collects all wash buffers once passed through the LFC 148. FIG. 11C shows another design of a multi-chamber cartridge. In this design, multiple reaction chambers 10 share a single waste chamber 60.

Detection Module 140

The detection module 140 detects the presence of the molecules of interest in the reaction chamber. In some embodiments, the molecules of interest comprise the reaction product of an amplification reaction, such as a polymerase chain reaction (PCR). In certain embodiments, the detection module 140 comprises an optical subsystem designed to capture images of the microarray in the reaction chamber. In certain embodiments, the optical subsystem is specifically designed for low-level fluorescence detection on microarrays. The optical subsystem uses confocal or quasi-confocal laser scanners that acquire the microarray image pixel by pixel in the process of interrogating the object plane with a tightly focused laser beam. The laser scanners offer the advantages of spatially uniform sensitivity, wide dynamic range, and efficient rejection of the out-of-focus stray light. In some embodiments, the detection module 140 is capable of real time monitoring of the amplification reaction in the reaction chamber of a LFC. In certain embodiments, the detection module 140 comprises an optical subsystem with a laser light source.

In another embodiment, the optical subsystem uses imaging devices with flood illumination, in which all of the microarray elements (features) are illuminated simultaneously, and a multi-element light detector, such as a CCD camera, acquires the image of microarray either all at once or in a sequence of a few partial frames that are subsequently stitched together. Compared to laser scanners, CCD-based imaging devices have simpler designs and lower cost. CCD-based imaging systems are an attractive option for both stand-alone and built-in readers in cost-sensitive applications relying on microarrays of moderate complexity (i.e., having a few hundred or fewer array elements). Commercial instruments typically use cooled CCD cameras and employ expensive custom-designed objective lenses with an enhanced light-collection capability that helps to balance, to some extent, the low efficiency of the excitation scheme.

In another embodiment, the optical subsystem contains an imaging device that uses a non-cooled CCD camera. Although non-cooled cameras typically have a noticeably higher dark current as compared to the cooled models, the optical subsystem could provide the required sensitivity without using exposures in excess of a few seconds by (1) increasing the excitation intensity, or (2) employing an objective lens with high light collection efficiency; or (3) using the above two approaches in combination. The light source can be a conventional light source, such as a metal halide or mercury bulb, a laser-based system, or a high-intensity LED.

In another embodiment, the optical subsystem has a fluorescence-independent imaging (FII) mode as a supplementary imaging mode of microarray reader operation. The FII mode allows imaging the array elements regardless of their fluorescence level.

The practical implementation of FII is technically challenging in both microarray scanners and imagers using flood illumination. The problem is especially difficult when the microarrays to be imaged are the mainstream planar arrays, because the layer of biomolecular probes immobilized on the microarray substrate is too thin to produce a noticeable change in the intensity of light used for probing the slide surface.

In one embodiment, the present invention uses dark field illumination in reflected light for imaging gel arrays printed on opaque (black) plastic substrates. In another embodiment, the present invention uses oblique illumination in transmitted light for imaging gel arrays printed on transparent (glass) slides. In both cases, the light source used for FII could be any light source emitting within the transmission band of the imager's emission filter.

EXAMPLES

Example 1: Analysis of Arrays

In order to test the sample handling and imaging of the microarray imaging positioning device disclosed herein, a series of test arrays were printed. Briefly, the following steps were used for printing the test microarrays: (1) an oligonucleotide mixture was prepared and dried down on a CentriVap. (2) A copolymer solution comprising monomer, cross-linker, glycerol and buffer was prepared. (3) The dried oligonucleotide was dissolved in the copolymer solution. (4) The oligonucleotide-copolymer solution was placed into a source plate, and (5) the source plate was used for array printing/polymerization/washing.

Figure 12:
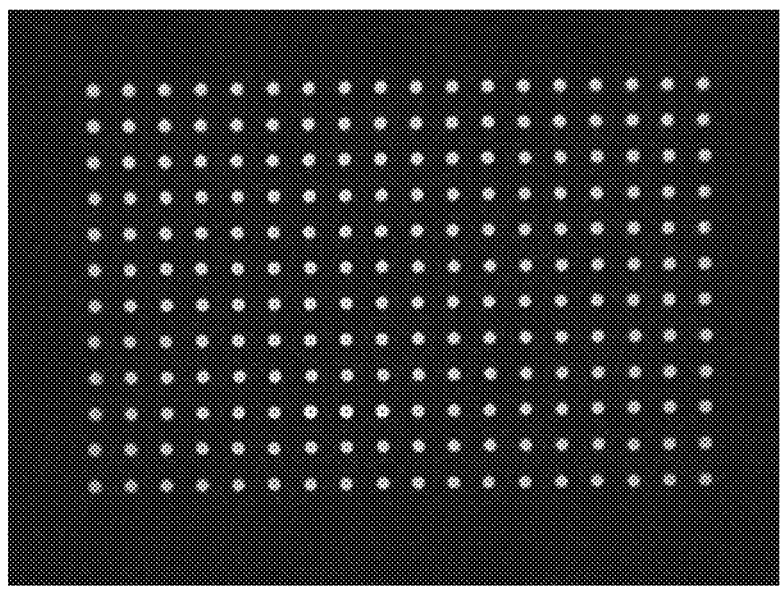
FIG. 12 shows a control uniform array labeled with Cy3.

FIG. 12 shows a uniform 12×18 microarray labeled with identical concentrations of cyanine Cy3 dye. The array was imaged using the microarray imaging positioning device comprising a stage and a rotatable carousel depicted in FIGS. 9A-9B.

Figure 13:
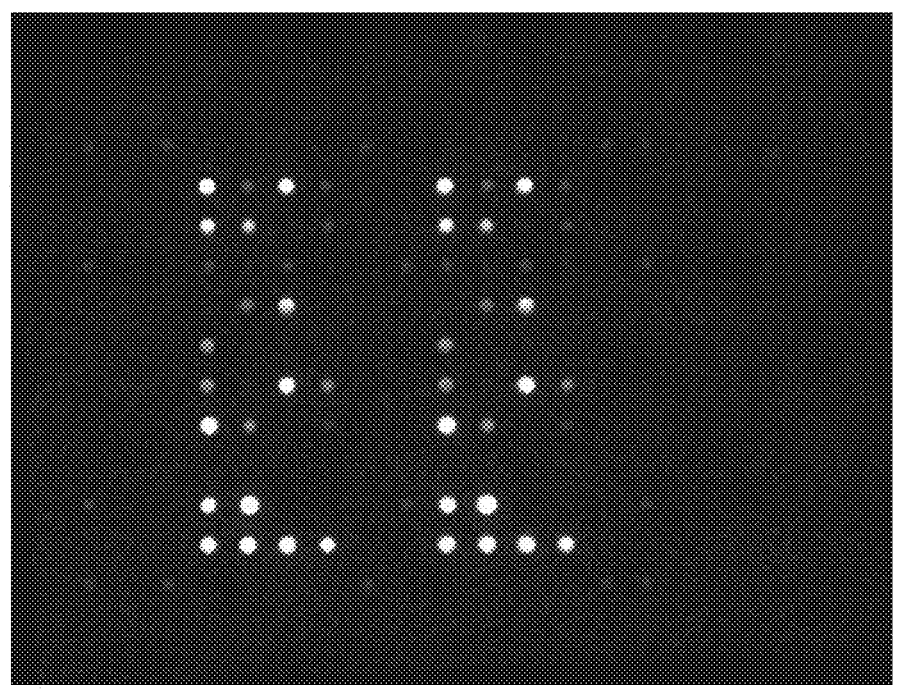
FIG. 13 shows a test Mycobacterium tuberculosis (TB) array imaged using the positioning module embodiment depicted in FIGS. 9A-9B.

FIG. 13 shows an image of a Mycobacterium tuberculosis (MTB) microarray printed on a substrate as a component of an LFC. The MTB microarray is imaged with the positioning device for microarray imaging comprising a stage and a rotatable carousel depicted in FIGS. 9A-9B. In this case, the capture instrument was running Akonni AMA software.

Figure 14:
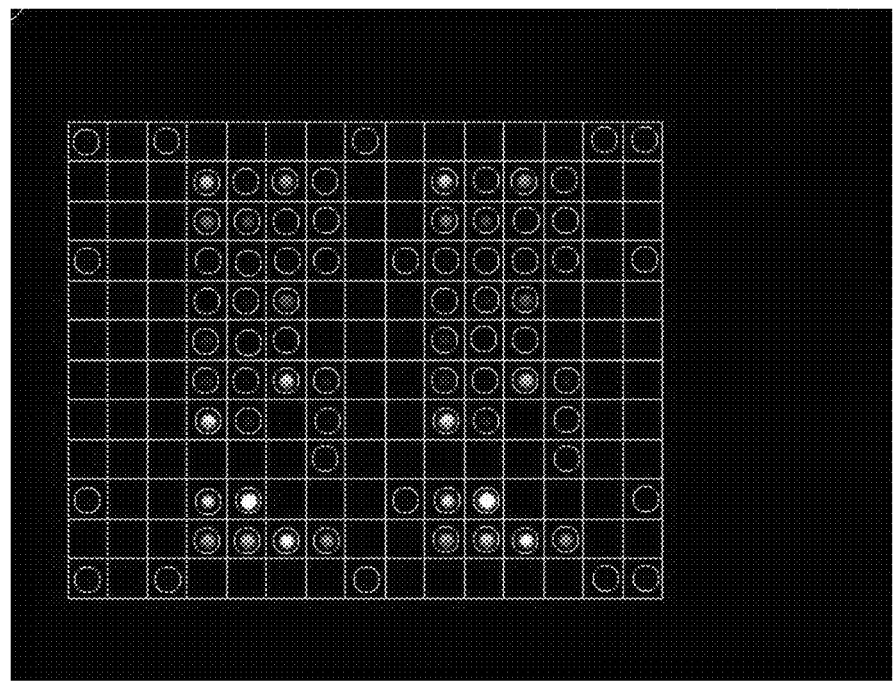
FIG. 14 shows processing of the array of FIG. 13 using automated microarray analysis (AMA) software.

FIG. 14 shows the array of FIG. 13 after processing by Akonni AMA software. The superimposed grid shows the results of automated spot detection, wherein a circle within a grid indicates the location of a microarray spot.

Example 2: Sample Purification Device

Figure 15:
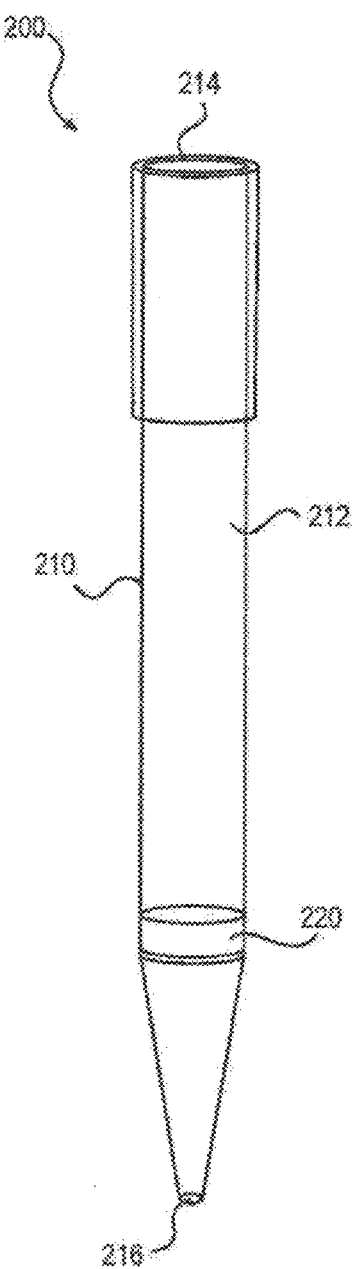
FIG. 15 shows an embodiment of a sample purification device of the present application.

FIG. 15 shows an embodiment of a sample purification device 200 that includes a housing 210 and a sample filter 220. The housing 210 defines a sample passageway 212 between a first opening 214 and a second opening 216. The shape and size of the housing 210 are not particularly limited. In this embodiment, the preferred housing configuration is substantially cylindrical so that the flow vectors during operation are substantially straight. In the embodiment shown in FIG. 15, the housing 210 has a pipette tip geometry, i.e., the first opening 214 has a diameter that is greater than the diameter of said second opening 216, and the first opening 214 is dimensioned to fit onto the tip of a pipette.

The sample filter 220 is placed in the close proximity of the second opening 216 so that samples are filtered immediately after being taken into the housing 210 through the second opening 216. In one embodiment, the sample filter 220 is contiguous with the second opening 216. In another embodiment, the sample filter 220 is separated from the second opening 216 by a distance of 1-20 mm. In some embodiments, the monolith sample filter is a glass frit with an average pore size of 20-200 micron. In another embodiment, the sample filter 220 is a monolith filter with two sections having different porosities: a first section at the proximity of the second opening 216 and a second section that is separated from the second opening 216 by the first section 221. In one embodiment, the first section has an average pore size of 40-200 micron, preferably 40-60 micron, and the second section has an average pore size of 1-40 micron, preferably 1-20 micron.

Example 3: Heating and Cooling Device

Figure 16A:
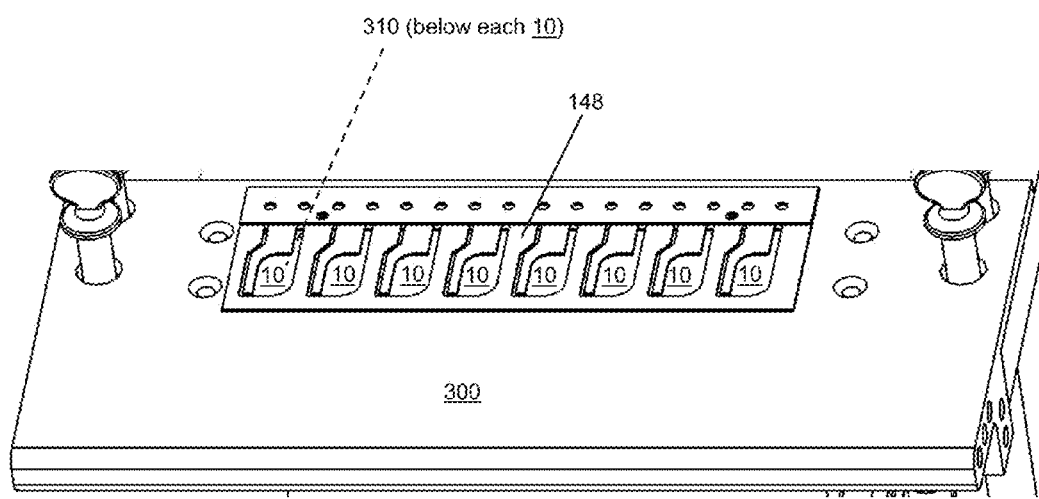
FIGS. 16A and 16B show embodiments of the heating and cooling device with LFCs resting on top of the heat spreader (FIG. 16A) or below the heat spreader (FIG. 16B).
Figure 16B:
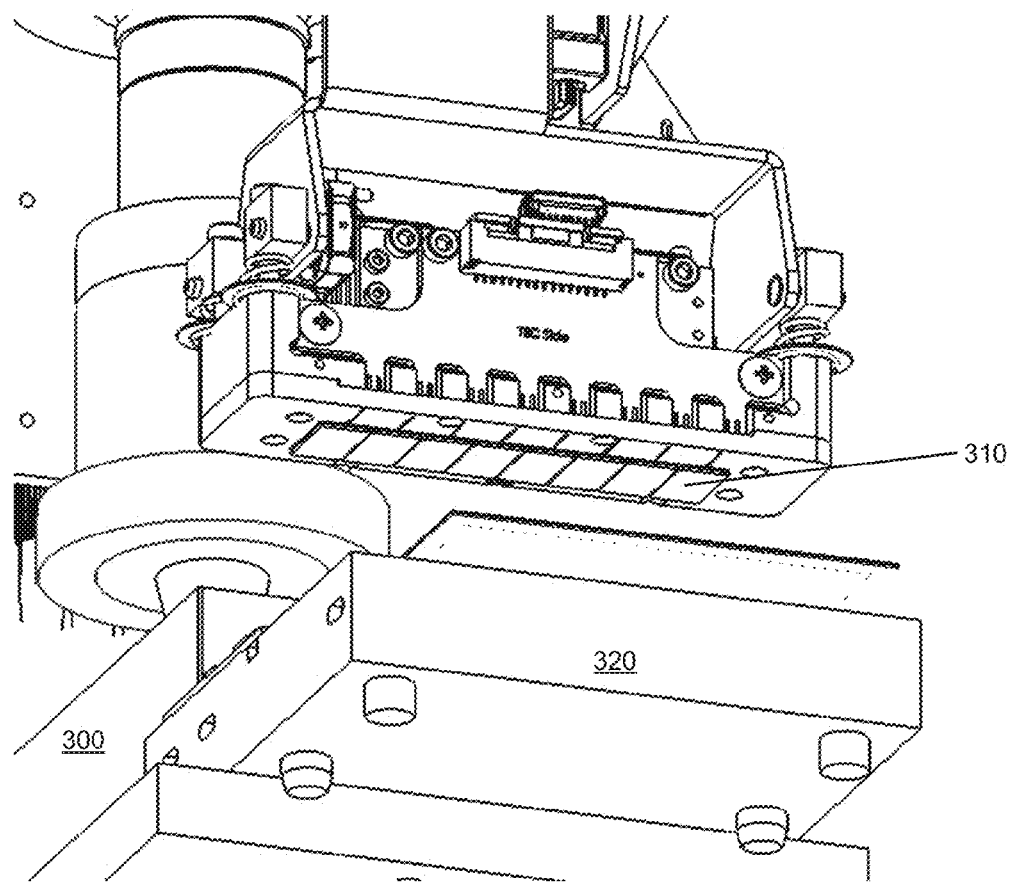

FIGS. 16A-16B show an embodiment of a heating and cooling device 300 in the temperature control module 120, which provides both heating and cooling functions based upon switching the current. In some embodiments, the cartridge 146 disengages from the heating and cooling device 300 before centrifugal drying and imaging. In other embodiments imaging occurs simultaneously with heating or cooling to allow real-time monitoring e.g., nucleic acid amplification in the reaction chamber. The heating and cooling device 300 includes one or more heat spreaders 310 that are adapted to make contact with an exterior surface of the reaction chamber 10 of the LFC 148, and one or more thermoelectric devices. In some embodiments, the thermoelectric device is a Peltier device made of ceramic materials, which provides both heating and cooling functions based upon switching the current. In other embodiments, the thermoelectric device is a thin film semiconductor (e.g., Bismuth Telluride), which provides both heating and cooling functions based upon switching the current. In other embodiments, the thermoelectric device is a thermoelectric couple made of p and n type semiconductors, which provides both heating and cooling functions based upon switching the current.

In some embodiments, the thermoelectric device has a heat sink coupled to one side and a heat spreader coupled to the other side. Exemplary heat sinks and heat spreaders include copper, aluminum, nickel, heat pipes, and/or vapor chambers. During operation, the heat spreader makes intimate contact with an exterior surface of the reaction chamber and controls the temperature inside the reaction chamber. In some embodiments, the heating-and-cooling module further comprises a fan under the heat sink. In one embodiment the heat spreader is flat. In some of these embodiments the heat spreader is rectangular with dimensions that range from 3 mm×3 mm to 20 mm×20 mm. The thickness of the heat spreader is preferably 0.05 to 5 mm, and more preferably 0.1 to 0.5 mm, and even more preferably 0.15 to 0.3 mm.

In some embodiments, the heating and cooling device 300 further comprises a temperature sensor. Exemplary temperature sensors include resistance thermal devices (RTDs), thermocouples, thermopiles, and thermistors.

In some embodiments, the LFCs 148 are located on top of the heat spreader (FIG. 16A). In some embodiments the heat spreader absorbs light. Examples of how to achieve light absorption include painting the heat spreader black, black anodizing, or coating it with black chrome. Light absorption reduces scatter that can interfere with imaging microarrays. In some embodiments, thermocycling occurs prior to imaging. In some embodiments thermocycling occurs simultaneously with imaging.

In other embodiments, the LFCs 148 are located below the heat spreader 310. The heat spreader 310 is adapted to descend onto the reaction chamber 10 of the LFC 148 (FIG. 16B). Alternatively, the platform 320 may ascend to bring the LFC 148 in contact with the heat spreader 310.

In other embodiments two or more heat spreaders interface with each reaction chamber. An example of this is that one heat spreader interfaces with the top of the reaction chamber while another heat spreader interfaces with the bottom of the reaction chamber.

Example 4: Optical Subsystem with Oblique Angle Illumination

Figure 17A:
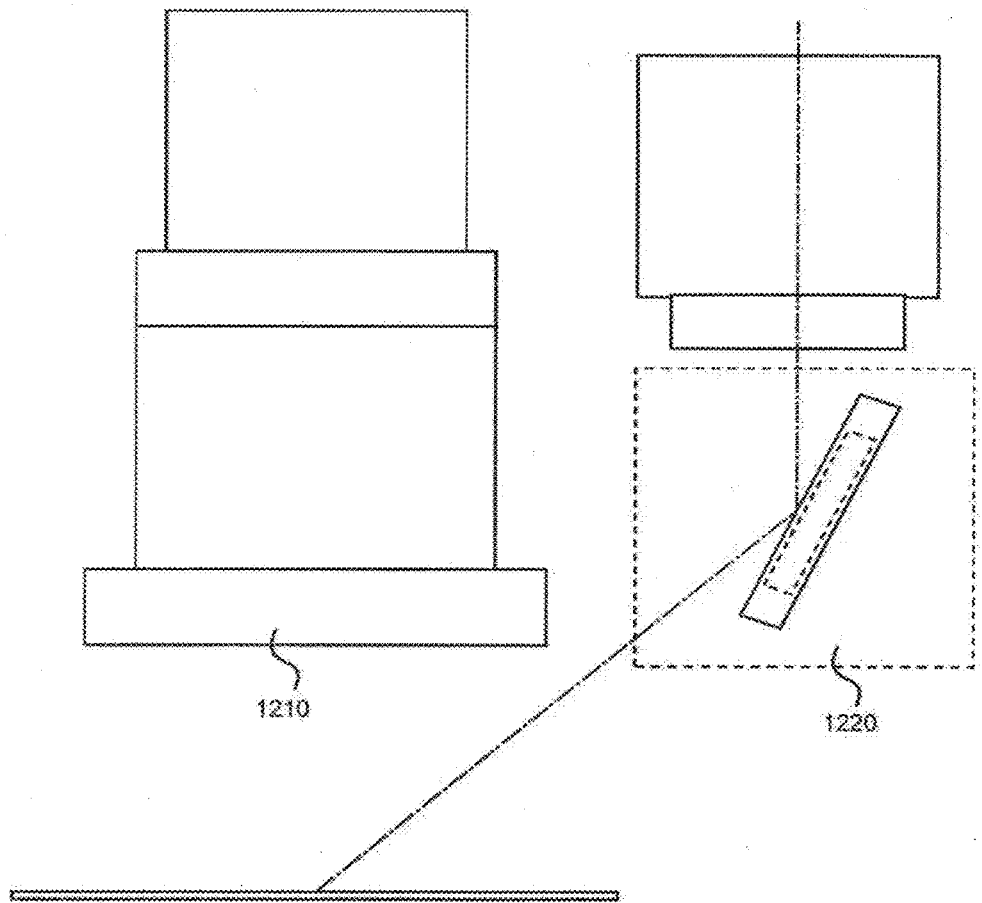
FIGS. 17A-17C show an embodiment of the optical subsystem.
Figure 17B:
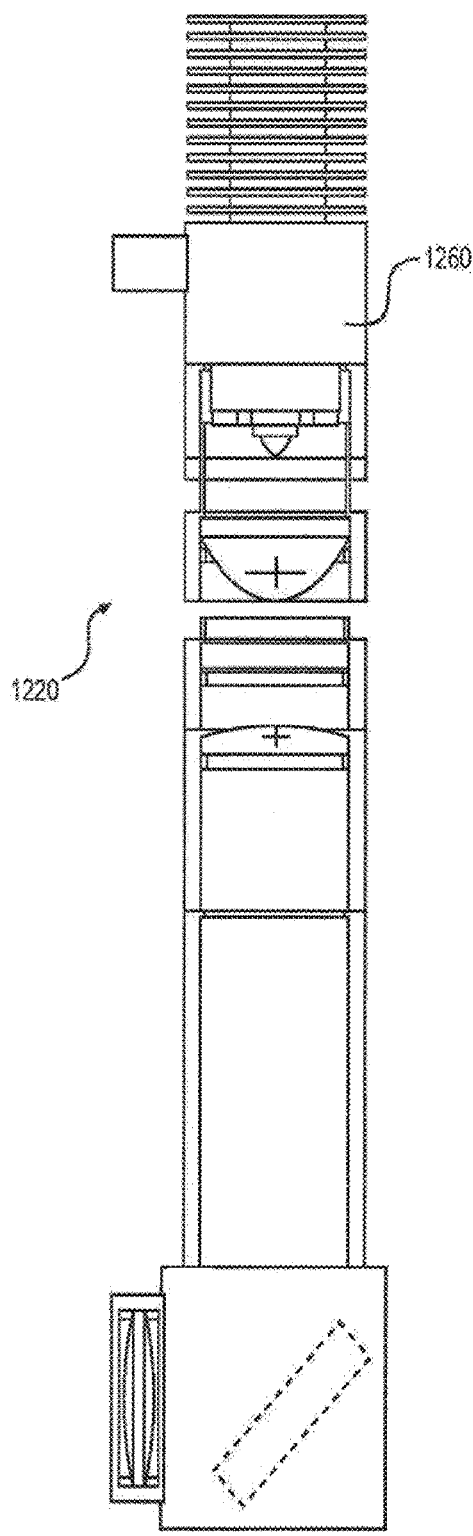
Figure 17C:
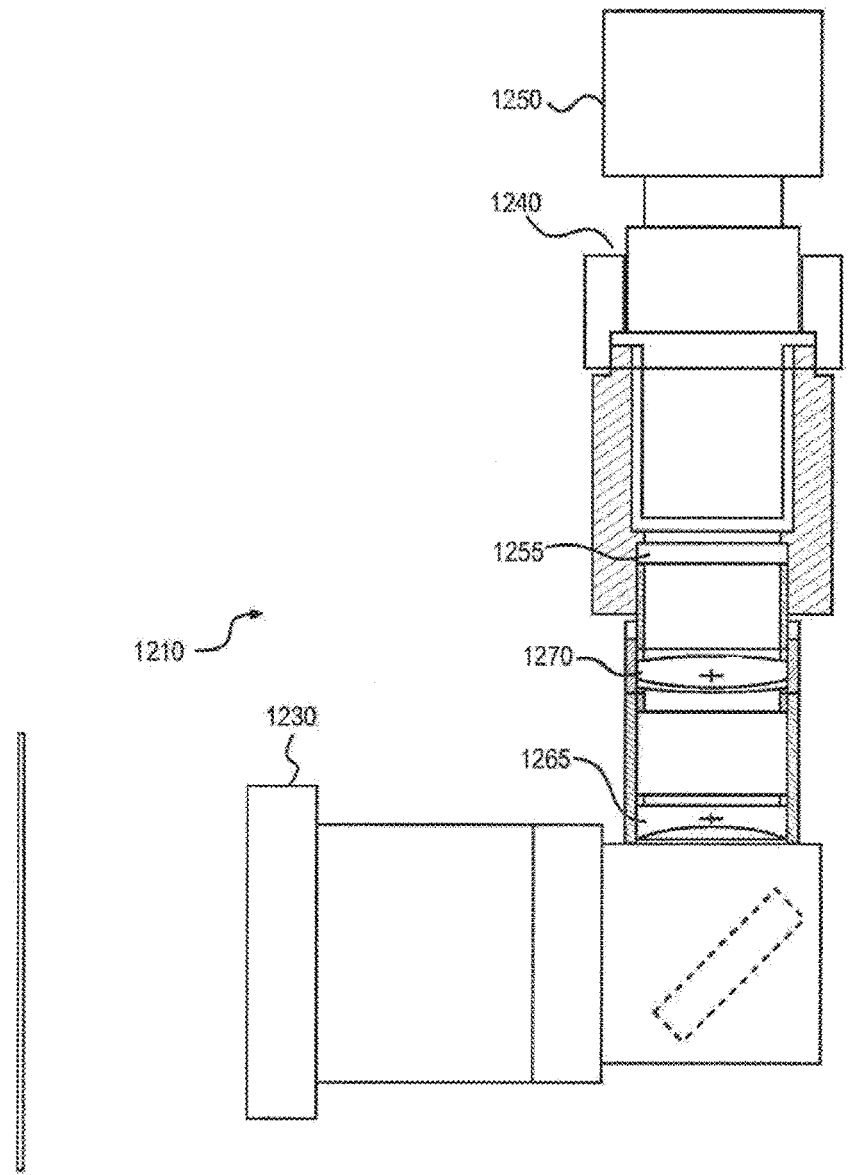

FIGS. 17A-17C show an embodiment of an optical subsystem with oblique angle illumination for microarray imaging schemes. FIG. 17A shows the general concept of oblique angle illumination for microarray imaging. The system's optical train comprises two separate channels 1210 and 1220. Channel 1220 is used for fluorescence excitation and channel 1210 is used for imaging the array. FIG. 17B is an embodiment of the illumination optical train that includes a mirror to divert the illumination source at a 90 degree angle to allow a significant portion of the illumination optics to be parallel to the microarray substrate. FIG. 17C is an embodiment of the collection light optical train that includes a mirror to divert the collection light at a 90 degree angle to allow a significant portion of the detection optics to be parallel to the microarray substrate.

As shown in FIGS. 17B and 17C, the optical train includes high-quality imaging optics (an objective lens 1230 and a matching video lens 1240), a compact low-noise monochrome ⅓" CCD camera 1250, and a 530 nm high-intensity LED as a fluorescence excitation source 1260. In contrast to the commonly-used fluorescence microscopy epi-illumination scheme, in which the objective is used for both illuminating and imaging the object, this design eliminates the background due to both the excitation light back-scattered in the objective and the possible optics auto-fluorescence. Also, oblique illumination at a 45° incidence angle helps to direct the major portion of the excitation light reflected from the microarray substrate away from the objective lens. Since the objective is infinity-corrected, the array surface of the slide should be positioned at the front focal plane of the lens. The emission filter 1255 is located in the infinity space between the objective and video lens and two-component beam expander comprising a plano-concave lens 1265 and an achromatic doublet 1270. The beam expander (not shown) reduces the magnification factor of the entire lens system to 0.75×. With the current CCD sensor having ⅓" format and a 7.4 µm pixel size, this magnification adjustment allows imaging a microarray with up to 12×18 gel elements at a spatial resolution (limited by the CCD array pixel size) of about 10 µm. The fluorescence excitation channel implements the Köhler illumination scheme for a projection system, which ensures uniform (within 3%) illumination of the object plane despite the complex structure of light emitting region of the LED. The bandpass cleanup filter placed between the collector and condenser lenses cuts off long-wavelengths of the LED emission spectrum that overlaps with the fluorescence band of Cy3. In some embodiments, the optical subsystem is configured to allow real-time imaging of a microarray in a reaction chamber.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A positioning system for a sample analysis device, comprising:
    a carousel comprising a platform and a sample loading tray mounted on the platform wherein the sample loading tray is configured for holding a cartridge comprising one or more lateral flow cells, wherein the one or more lateral flow cells (LFCs) include a reaction chamber in fluid communication with a waste chamber, the waste chamber includes a liquid-retaining absorbent; and
    a stage comprising a positioning system for positioning said carousel, wherein the carousel is rotatable relative to the stage;
    wherein the rotation of the carousel produces centrifugal forces sufficient to drive water droplets from the reaction chamber in the LFCs toward the liquid-retaining absorbent in the waste chamber; and
    wherein the carousel further comprises a clamp comprising a top bar, a bottom bar, and at least one supporting rod connecting the top bar and the bottom bar, wherein the platform and the sample loading tray are disposed between the top bar and the bottom bar of the clamp, wherein the clamp is movable relative to the platform and configured to secure the cartridge in the sample loading tray when the clamp is moved to a lock position,
    wherein the bottom side of the carousel comprises a magnet that facilitates movement of the clamp.

2. The positioning system of claim 1, wherein the carousel further comprises a handle configured to manually rotate the carousel.

3. The system of claim 1, wherein the stage further comprises a positioning system for X, Y and Z axis positioning, and angular adjustment of the carousel.

4. The system of claim 1, further comprises a heating and cooling device that is capable of heating and cooling the LFCs in the cartridge.

5. The system of claim 4, wherein the heating and cooling device is configured to allow real-time monitoring of a biochemical amplification reaction within a reaction chamber of an LFC of the cartridge by an imaging device.

6. The system of claim 1, wherein the carousel is movable to a reaction position to bring the cartridge into contact with a heating and cooling device to facilitate reactions in a reaction chamber of an LFC within the cartridge.

7. A positioning system for a microarray imaging device, comprising:
    a carousel comprising a platform and a sample loading tray mounted on the platform wherein the sample loading tray is configured for holding a cartridge comprising one or more lateral flow cells, wherein the one or more lateral flow cells (LFCs) include a reaction chamber in fluid communication with a waste chamber, the waste chamber includes a liquid-retaining absorbent; and
    a stage comprising a positioning system for X, Y, Z axis positioning said carousel, wherein the carousel is rotatable relative to the stage;
    wherein the rotation of the carousel produces centrifugal forces sufficient to drive water droplets from the reaction chamber in the LFCs toward the liquid-retaining absorbent in the waste chamber; and
    wherein the carousel further comprises a clamp comprising a top bar, a bottom bar, and at least one supporting rod connecting the top bar and the bottom bar, wherein the platform and the sample loading tray are disposed between the top bar and the bottom bar of the clamp, wherein the clamp is movable relative to the platform and configured to secure the cartridge in the sample loading tray when the clamp is moved to a lock position,
    wherein the bottom side of the carousel comprises a magnet that facilitates movement of the clamp.

8. The positioning system of claim 7, wherein the carousel further comprises a handle configured to manually rotate the carousel.

9. The system of claim 7, wherein positioning system of the stage further allows for angular adjustment of the stage.

* * * * *